(12) United States Patent
Berreklouw

(10) Patent No.: US 6,524,322 B1
(45) Date of Patent: Feb. 25, 2003

(54) ANASTOMOSIS DEVICE

(76) Inventor: Eric Berreklouw, Ardennenlaan 13, NL-5691 JN Son (NL)

( * ) Notice: Subject to any disclaimer, the term of this patent is extended or adjusted under 35 U.S.C. 154(b) by 0 days.

(21) Appl. No.: 09/807,685

(22) PCT Filed: Oct. 22, 1999

(86) PCT No.: PCT/NL99/00658
§ 371 (c)(1), (2), (4) Date: Apr. 23, 2001

(87) PCT Pub. No.: WO00/24339
PCT Pub. Date: May 4, 2000

(30) Foreign Application Priority Data

Oct. 23, 1998 (NL) .............................................. 1010386

(51) Int. Cl.[7] .............................. A61F 2/06; A61B 17/11
(52) U.S. Cl. ..................................................... 606/153
(58) Field of Search ......................................... 606/153

(56) References Cited

FOREIGN PATENT DOCUMENTS

| WO | WO 9803118 | 1/1998 | | |
|---|---|---|---|---|
| WO | WO 9803118 A1 | * | 1/1998 | ........... A61B/17/11 |
| WO | WO 9840036 | | 9/1998 | |
| WO | WO 9840036 A1 | * | 9/1998 | ............. A61F/2/06 |

* cited by examiner

*Primary Examiner*—Gregory Huson
*Assistant Examiner*—Lina Kontos
(74) *Attorney, Agent, or Firm*—Handal & Morofsky

(57) ABSTRACT

The invention relates to an anastomotic device for joining one end of a graft vessel to a target vessel at an opening made in the wall thereof The anastomotic device comprises a tubular body on which an outer flange, which comes into contact with the outside of the wall of the target vessel around the opening, and an inner flange, which comes into contact with the inside of the wall of the target vessel around the opening, are arranged. The inner flange is made up of a number of arms which are able to move from an extended position, located in the extension of the tubular body, under the influence of a pretension into a position extending in the lateral direction with respect to the tubular body, after the pretension has been released, in order to form the inner flange. The invention further relates to an anastomotic device comprising a tubular body with an outer flange and an inner flange thereon, the outer flange and optionally also the inner flange being cylindrically curved with a radius of curvature approximately equal to the radius of curvature of the target vessel.

32 Claims, 17 Drawing Sheets

ANASTOMOSIS DEVICE

The present invention relates to an anastomotic device for joining a graft vessel to a target vessel at a connection opening present therein.

Anastomoses can in the general sense be subdivided into three types: so-called "end-to-side anastomoses" (abbreviated as ETS anastomoses), so-called "side-to-side anastomoses" (abbreviated as STS anastomoses) and so-called "end-to-end anastomoses" (abbreviated as ETE anastomoses). The anastomotic device according to the invention can be used with any of these three types of anastomoses. An ETS anastomotic is understood to be an anastomotic where one end of one vessel, the graft vessel, is joined to an opening formed in the wall of another vessel, the target vessel. A sort of T-join is thus produced. An STS anastomotic is understood to be an anastomotic where the two vessels to be joined each have an opening formed in their wall, which openings are joined to one another. A so-called ETE anastomotic is understood to be an anastomotic where t-o vessels are joined to one another by joining two vessel ends to one another. This is, as it were, a continuous join where the vessels are located in the extension of one another, for example straight or obliquely at an angle with respect to one another.

According to the invention, the connection opening can thus be either a side opening made in the wall of the target vessel in the case of an ETS or STS anastomotic or an end opening in the case of an ETE anastomotic. The end opening will then be determined by the cutting plane along which the target vessel has been cut through at its end.

According to the invention, the graft vessel and target vessel in this context are in particular blood vessels, but they can also be other hollow tubular organs, such as the urethra, Fallopian tubes, etc. Within the framework of the present invention, the terms graft vessel and target vessel are used as distinguishing terms which serve to distinguish between a first vessel (the graft vessel) and a second vessel (the target vessel). The terms graft vessel and target vessel are thus in no way intended to restrict the invention. Throughout this entire application the terms target vessel and graft vessel can in many cases be interchanged without going beyond the scope of the invention.

Graft vessels which are used in practice and can also be used according to the invention are, inter alia:
- the vena saphena magna, which is usually completely detached as a free graft (transplant), but in peripheral vascular surgery is also left in the anatomical position as a so-called in situ graft and joined to neighbouring leg arteries;
- the vena saphena parva, which is usually used for transplant purposes and to this end is completely detached;
- veins from the arms, which are usually used for transplant purposes;
- the arteria thoracica interna, which is usually detached only caudally and is sometimes used as a free graft;
- the arteria radialis from the arm, which is used as a free graft;
- the arteria gastro-epiploica dextra, which usually is detached only caudally on the spleen side (transponate) and sometimes is used as a free graft;
- arteria epigastrica inferior, which in general is used as a free graft;
- vessel prostheses made of plastic;
- veins or arteries of animal or human material, which in general are stored in the frozen state.

An anastomotic device according to the invention can, for example, be used when making a by-pass in the case of, for example, a blocked coronary artery of the heart. By-pass operations of this type are carried out on a large scale and to date the graft vessel has been attached to the target vessel entirely by hand. In this case in general an opening is made in the aorta wall, where one end of the graft vessel is attached to the edges of the opening by stitching by hand. This join is termed the proximal anastomotic with the aorta. The other end of the graft vessel is joined by hand to the coronary artery beyond the blockage in a corresponding manner by means of suturing. The latter join is also termed the distal anastomotic with the coronary artery. An experienced surgeon is able to complete one anastomotic by suturing in approximately 10 minutes.

Most by-pass operations are also performed using a heart-lung machine, the heart then being temporarily stopped. Since stopping the heart in this way can not only be harmful for the heart itself (after all, the heart no longer has a blood supply) but also for other organs and bodily functions it is important that the time for which the heart is stopped is as short as possible. According to a recent development attempts are being made to perform an increasing number of operations on the beating heart, that is to say without heart-lung machine and without stopping the heart. The reason for this is that operations on the beating heart should be less harmful to the heart and other organs and are much less expensive. In the case of such by-pass operations on the beating heart, the bloodstream is temporarily interrupted at the location of a coronary artery to be by-passed. Also in the case of such a by-pass operation on the beating heart it is extremely important that the interruption to the bloodstream lasts for as short a time as possible, since otherwise a cardiac infarction can occur at this site. An ancillary problem in the case of by-pass operations on a beating heart is that the heart usually has to be lifted in order to be able to reach coronary arteries at the side and bottom of the heart, which in general is poorly tolerated by the heart and can lead to a fall in blood pressure or stoppage of the heart. An anastomotic which can be completed rapidly would make such an operation much more possible.

In addition to the recent development for performing an increasing number of heart operations, such as by-pass operations, on the beating heart, there is also an increasing number of operations which are performed via a small access route or thoracoscopically, there then being little or no possibility for suturing by hand. The aim of the present invention is to provide an aid with which joining of a graft vessel onto a target vessel can be completed in a reliable and reproducible manner, efficiently and with minimum stress on the patient. Said aim is achieved by the provision of accessories with which the conventional, relatively labour-intensive, lengthy and, as far as the result is concerned, less predictable suturing carried out by the surgeon on the body of the patient can be avoided or at least restricted to a minimum.

WO 96/25886, which discloses an anastomotic device of the type mentioned at the beginning, proposes a large number of diverse accessories for the same purpose. The starting point here is the philosophy that there must be no contact between the blood and foreign materials, the corollary of which is the aim to shield all accessories as far as possible by vascular wall material towards the interior of the vessels. However, the measures taken for this purpose—i.e. covering all or as many as possible internal, foreign parts with the aid of the wall of the graft vessel—result in a decrease/constriction in the flow aperture available for blood.

The accessories from WO 96/25886 each also have numerous other disadvantages. In many cases the graft vessel has to be stretched, which is possible to only a limited extent or is not possible or is possible only by constricting the graft vessel in another location. Furthermore, with many accessories the wall of the target vessel is punctured by so-called staples. These staples can be driven through the wall of the target vessel from the outside to the inside or driven through the wall of the graft vessel from the inside to the outside by folding arms outwards. Instruments for bending the staples are needed for driving the staples through the wall, both from the inside to the outside and from the outside to the inside. The requisite forces are exerted during this operation, inter alia on the target vessel. When a staple has to be driven through the wall from the outside to the inside in the case of a calcified diseased vessel there is a risk of the staple pushing the wall of the calcified, diseased vessel ahead of it, as a result of which the staples are not able to engage adequately on the wall of the vessel. In the case, in WO 96/25886, of the staples going from the inside to the outside, they usually penetrate both the wall of the aorta or coronary artery (the target vessel) and the wall of the graft vessel. If manipulation has to be from the inside of the target vessel in order to drive the arms and the staples connected thereto through the wall of the target vessel from the inside to the outside, an instrument has to be introduced into the target vessel either via the target vessel or via the graft vessel to be attached. If the graft vessel has already been joined by its other end to another target vessel, this implies an additional surgical intervention in the sense that the instrument has to be brought to the inside somewhere through the wall of a blood vessel and that, on completion, the opening made in a wall for this purpose has to be closed again. If parts of the accessories according to WO 96/25886 are introduced through the opening in the wall of the aorta or coronary artery, the target vessel, said parts usually have circumferential dimensions larger than those of the opening, which implies that the wall of the aorta or coronary artery must allow stretch, at the location of the opening, for introduction of the parts and that the opening must then reduce in size again. Especially in the case of diseased vessels this will generally be unsuccessful or the wall will tear or the opening will permanently remain too large. Furthermore, in WO 96/25886 all openings and all accessories are essentially round, which will give rise to problems when joining a graft vessel to a coronary artery. In general the diameter of the graft vessel is appreciably larger than that of the coronary artery or the target vessel. In the case of the circular or perfectly round ring shape this difference in diameter will give rise to joining problems and be able to impede the ability of the blood vessel to allow passage. After all, the target vessel has a restricted width which can be stretched to only a limited extent.

U.S. Pat. No. 4,350,160 discloses an aid for joining one end of a graft vessel to one end of a coronary artery. The method followed in this case is laborious. A further disadvantage is that the coronary artery has to be cut through transversely and that this fragile coronary artery then has to be bent around a component of the aid instrument. The graft vessel is also bent round, after which the two parts are stapled to one another.

Furthermore, WO 84/00102 discloses an apparatus for joining vessels to one another end-to-end. In this case as well the coronary artery has to be cut through transversely and then folded over a number of pins, which in practice proves to be difficult if not impossible, certainly in the case of very small vessels, such as coronary arteries.

U.S. Pat. No. 5,234,447 discloses an anastomotic device consisting of a ring with staple arms facing downwards from the bottom edge and further staple arms, flanged at their free ends, upright from the top edge. The graft vessel is inserted by its end to be attached, through the ring from top to bottom. Said free end is folded up towards the outside, after which the bottom staple arm is pushed through the folded-over part in order then to be bent round outwards and upwards, after which the entire anastomotic device with graft vessel is pushed into an opening formed in the wall of the target vessel, after which, finally, the bottom staple arms and top staple arms are pushed in the opposite direction through the tissue of the wall of the target vessel surrounding the openings in the target vessel and remain behind with their free pointed ends in said wall tissue of the target vessel. If the tissue of the target vessel is impaired, an anastomotic device of this type is not as suitable for use because of the puncturing of the wall tissue by the staple arms. A further problem can be that if the tissue of the wall of the target vessel is impaired said tissue could also easily tear away, which renders the join unreliable. Moreover, in this case the introduction/insertion into the target vessel will be difficult since the staples on the bottom edge have a diameter larger than that of the opening in the target vessel.

U.S. Pat. No. 4,366,819 discloses a four-part anastomotic device. Said anastomotic device consists of a round, tubular body through which that end of a graft vessel which is to be joined is inserted in order to be wrapped by its free end around the bottom rim of the tubular body. The wrapped-round section is fixed on the tubular body by means of a ring of triangular cross-section. To this end said ring is provided with point-shaped elements which face radially inwards and engage in the wrapped-round section of the graft vessel. Said prepared whole is inserted through an opening in the wall of a target vessel, after which the ring of triangular cross-section is inserted with its sloping top face in contact with the inside of the wall of the target vessel. An outer flange is pushed over the tubular body on the outside of the target vessel, which outer flange is provided with point-shaped elements which face in the longitudinal direction of the target vessel and are inserted in the wall of the target vessel from the outside. The outer and the inner flange are held clamped on one another by a fourth separate component in the form of a ring which can be fixed on the tubular body by means of interior serrations, which interact with exterior serrations provided on the tubular body, in such a way that the compression of tissue between the inner flange and outer flange is maintained. The disadvantage of this construction is that the inner flange already has its outward-facing shape, required for the flange action, before it is inserted in the target vessel and insertion of the prepared whole in the target vessel is thus made more difficult. After all, the diameter of the whole to be inserted inwards is greater than the diameter of the opening in the target vessel.

U.S. Pat. No. 4,368,736 discloses an anastomotic device with which one end of a connecting tube of non-tissue material is inserted in that end of the graft vessel that is to be joined and the other end is inserted in an opening made in the wall of the target vessel. During this operation the graft vessel and target vessel remain some distance apart. With this arrangement the connecting tube can have a bend so that, on the one hand, the connecting tube can be fitted at right angles to the target vessel and, on the other hand, the graft vessel can run at an angle with respect to the target vessel, at least some distance away from the target vessel.

WO 98/40036 discloses an anastomotic device consisting of essentially three basic components. The first basic component, termed 'attachment member 12', consists of a saddle-shaped inner flange with a branch tube, having a cylindrical passage, fixed thereto at an angle of 45° or 90°. The second basic component is the so-called 'clamp member 14', that forms a saddle-shaped outer flange and has a passage through which the branch tube can be inserted. The third basic component is the so-called 'locking member 16', which is a ring that is slidable over the branch tube. The graft vessel can be slid over the branch tube and clamped on the branch tube by means of the third basic component, the 'locking member'. WO 98/40036 does not specify precisely how the first basic component is placed in the target vessel. The saddle-shaped inner flange has dimensions which do not allow it to be inserted from the outside through the connection openings into the target vessel. The branch tube has the disadvantage that it protrudes into the graft vessel and that blood to be passed through the graft vessel will be in contact with the branch tube on flowing through said section of the branch tube.

An anastomotic device according to the precharacterising clause of claim 1 is disclosed in WO 98/03118. This PCT application relates to an "anastomotic fining" comprising a tubular body, an inner flange, which is provided at the bottom of the tubular body and can consist of arms with cut-outs between them or can be of folded construction, and a flat locking ring, which can be fitted around the tubular body on the outside and acts as outer flange. The way in which said anastomotic fitting is fitted is described from line 4 line 6 of WO 98/03118. For insertion, the arms of the inner flange are in an extended, axial position, the graft vessel is then inserted through the tubular body and the end of the graft vessel is folded back over the extended arms. The folded-back portion of the graft vessel is held in place by means of a locking sleeve. The end of the tubular body with extended arms and graft vessel folded back around them is inserted through an opening in the target vessel and a balloon located in the end with the extended arms is inflated to bend the arms from the axial, extended position (FIG. 6a in WO 98/03118) outwards (FIG. 6b in WO 98/03118) into a radial position (FIG. 6c in WO 98/03118). To fix the graft vessel on the target vessel the locking ring is slid downwards, pins provided on the locking ring penetrating the wall of the target vessel and the wall of that part of the graft vessel that has been folded back and subsequently folded radially outwards. In accordance with WO 98/03118 the inner flange is thus forcibly bent from the axial insertion position into the radial fixing position by means of a balloon. The use of such a balloon has the disadvantage that the latter not only has to be fed through the graft vessel but also that it has to be introduced somewhere via an access and also has to be removed again. This is awkward and complicated, especially if the graft vessel does not still have another free end, for example when said other end has already been fixed to another vessel.

The aim of the present invention is therefore in particular to provide an improved anastomotic device for joining a graft vessel to a target vessel at an opening present therein.

The abovementioned aim is achieved according to a first aspect of the invention by the provision of an anastomotic device for joining a graft vessel to a target vessel at a connection opening present therein, comprising:

an essentially tubular body having a bottom rim to be directed towards the target vessel;

an outer flange that is fitted or can be fitted on the outside of the tubular body and can be brought into contact, around the connection opening, with the outside of the wall of the target vessel; and an inner flange, formed on the tubular body, which in a free position projects outwards with respect to the tubular body and, overlapping the outer flange around the connection opening, can come into contact with the inside of the wall of the target vessel and which, during insertion of the inner flange in the target vessel, is in an essentially extended position with respect to the tubular body, the inner flange preferably being reversibly bent against a resilient force from the free position into a pretensioned position in which the projection thereof on the plane spanned by the bottom rim of the tubular body is essentially located on and/or inside said lower rim, such that the latter can be inserted through the connection opening in the target vessel, and is fixed in said pretensioned position in a manner such that the fixing can be released in order to bend the inner flange back in the direction of the free position under the influence of the pretension.

A significant advantage of the anastomotic device according to the invention is, on the one hand, that fixing to the target vessel takes place by clamping the tissue surrounding the connection opening between the inner flange and outer flange. The quality of the wall of the target vessel will thus have hardly any influence on the strength of the join of the anastomotic device with the target vessel. This is in contrast to joins based on staples, such as are known from the prior art. Another significant advantage of the anastomotic device according to the invention is that the inner flange is in an extended, parallel or optionally sloping, inward-facing, position when inserting the anastomotic device through the connection opening in the target vessel. What this amounts to is that the inner flange is thus not in a free position projecting outwards with respect to the tubular body, which means that that part of the anastomotic device which is to be inserted through the connection opening in the target vessel has a peripheral contour that is not larger than the peripheral contour of the opening in the target vessel. Thus, that part of the anastomotic device to be inserted in the target vessel fits in said connection opening. Stretching of the tissue of the target vessel around the connection opening or otherwise relatively complex manipulation in order to achieve insertion of the anastomotic device in the connection opening is therefore not necessary. All or part of the inner flange can be brought from the extended position into the outward-facing free position, in which it effectively forms the inner flange, with the aid of mechanical or other instruments. However, it is preferable if the inner flange is reversibly bent, against a resilient force, from the free position into a pretensioned position, that is to say during insertion of the anastomotic device into the connection opening the inner flange is a pretensioned, extended, or inward-facing, inner flange. The way in which this faces inwards can optionally be facing inwards at right angles, but in general the way in which it faces inwards will rather be, preferably gentle (i.e. <15°), tapering.

Such an anastomotic device with pretensioned, extended inner flange has the advantage that, when fitting the anastomotic device on the target vessel, the inner flange initially faces forwards essentially in the extension of the tubular body or inwards towards the axis of the tubular body (in particular tapers) and consequently can be easily inserted inwards through the connection opening of the target vessel. After the inner flange has been inserted through the connection opening in the target vessel in this way, the fixed, pretensioned position thereof can be released. The inner flange is then able to bend back again into its free position in which it projects, or at least tends to project, laterally with respect to the tubular body and that side thereof which faced outwards in the extended/fixed position comes into contact with the inside of the wall of the target vessel. Fixing to the target vessel is then produced by clamping the wall section of the target vessel located around the opening between the outer flange and the inner flange. If the inner flange has been made from a permanently resilient material, release of the inner flange from the fixed, pretensioned position (or extended position) can, for example, be achieved by pulling back a ring or sleeve fitted around the inner flange on the outside or by removing a cord or other form of restriction fitted around the inner flange. If necessary, it is possible to improve the contact of the inner flange with the inside of the wall of the target vessel by means of an instrument, for example by placing a balloon in the target vessel at the location of the join and inflating said balloon or by exerting mechanical pressure with the aid of another means in order thus to press the inner flange more firmly against the inside wall of the target vessel.

Yet a further significant advantage of the anastomotic device according to the invention is that the protrusion of tissue of the graft vessel into the lumen of the target vessel can be restricted to a minimum or even completely avoided by this means because virtually no internal parts inside the target vessel have to be covered by the graft vessel and neither the graft vessel nor the bottom rim of the tubular body protrudes into, or at least a significant extent into, the lumen of the target vessel.

A further significant advantage of the anastomotic device according to the invention is that when the anastomotic device has been fitted the clamping force exerted on the tissue around the connection opening in the target vessel can be uniformly distributed.

As already indicated at the beginning, the anastomotic device according to the invention can be used with all three types of anastomoses, that is to say ETS anastomoses, STS anastomoses and ETE anastomoses. In the case of an ETE anastomotic the inner flange will preferably face inwards when in the so-called extended position. In the so-called free position and assembled position it will be held in a position extending forwards or facing somewhat outwards by the outer flange (which in the assembled position is located on the outside around the target vessel). If the outer flange is absent and the inner flange is considered completely separately from the remainder of the anastomotic device, said inner flange can assume a shape which in the free position optionally faces radially outwards. In the assembled position said position facing radially outwards will not be able to arise because of the outer flange. In the case of an ETE anastomotic the outer flange will essentially be able to assume the shape of a tube, optionally a cylindrical tube.

In order to be able to facilitate fitting of the anastomotic device under certain conditions, it is advantageous according to the invention if the outer flange is a component which is separate from the tubular body and/or inner flange, is slidable in the longitudinal direction of the tubular body and/or in the direction of the inner flange and can be locked with respect to the tubular body and/or the inner flange by means of locking means. So as to be able, with this arrangement, in the case of an embodiment of the invention which is intended for joining to a target vessel of the type where the connection opening has been made in the wall (that is to say a so-called ETS or STS anastomotic), to adjust the clamping force with which the wall section of the target vessel surrounding the opening is clamped between the inner flange and outer flange it is advantageous according to the invention if the distance from the outer flange to the tubular body and/or the outward-projecting inner flange is adjustable. In this way it is possible, for example, to obtain a specific, desired clamping force depending on the thickness of the wall of the target vessel. In this context the adjustability can be continuous or discontinuous. According to an advantageous embodiment of the invention, the locking means comprise a mechanism involving serrations. If required, a mechanism of this type involving serrations can also be used to achieve adjustability of the distance from the outer flange to the tubular body and/or the outward-projecting inner flange. An ETE anastomotic can also be carried out in such a way that on sliding the outer flange in the longitudinal direction of the tubular body a compressive force is applied to the vessel wall and the vessel wall is thus clamped firmly between the outer flange and inner flange.

So as to restrict to a minimum, or even completely to avoid, the use of instruments having a mechanical action on the anastomotic device and/or the target vessel and/or the graft vessel, it is advantageous according to the invention if the inner flange is made from a superelastic metal alloy or a thermally activated or activatable alloy with shape memory, such as a nickel-titanium alloy. As an example of a nickel-titanium alloy, the material known by the trade name Nitinol can be used. Such a superelastic metal alloy or a thermally activated/activatable alloy with shape memory has the property that it can be brought from a free state, against a resilient action, into a deformed state and can be fixed in said deformed state by means of a treatment, in general a cold treatment. When said fixing is then released, for example by heating the material to above a certain temperature, the original resilience, which counteracts bending, will return and restore the inner flange to its original free state.

According to a further advantageous embodiment of the invention, the inner flange has a bending axis which extends tangentially with respect to the bottom rim of the tubular body and is located at the level of the inner periphery of the outer flange. What can be achieved in this way is that the anastomotic device does not protrude, or protrudes only slightly, into the target vessel when it has been fitted on the target vessel. Specifically, the inner flange then already bends in the opening via which it is inserted into the target vessel and can then come into flat contact with the inside of the wail of the target vessel from the inside and can even be pressed somewhat into the vessel wall, which consists of flexible material. Because the anastomotic device does not protrude, or hardly protrudes, into the target vessel, the blood flow through the target vessel will also not be impeded or disturbed by sections protruding into the target vessel.

According to a further particular embodiment, which, in particular, can also be used to obtain a bending axis of the inner flange at the level of the inner periphery of the outer flange, or even above this, the inner flange has a number of arms which are separated from one another by notches, cut-outs or folds and are arranged distributed around the periphery of the tubular body, the notches or cut-outs or folds preferably continuing as far as or beyond the outer flange. If the inner flange is made of arms separated from one another by notches or cut-outs, the inner flange can then be regarded as a discontinuous flange, the arms adjacent to one another in the peripheral direction always being separated from one another by notches or cutouts forming discontinuities. However, the flange can also be constructed as a continuous flange, for example by making this of folded construction, at least in the so-called extended or inward-facing position, in which case the outward-facing backs of the folds can be regarded as arms and the fold troughs located between said fold backs can be considered as folds. When the inner flange moves from its pretensioned position (the extended or inward-facing position) into its free position, the fold troughs will be pulled flat (or at least pulled up to a lesser fold trough depth) in order to make it possible for the inner flange to move into the free position and in doing so also to be able to create an uninterrupted inner flange contact surface.

In order to increase the grip of the inner flange on the inner wall of the target vessel it is advantageous according to the invention if that face of the inner flange which in the free position faces towards the inner wall of the target vessel is provided with roughening or unevenness. Said face of the inner flange can optionally also be provided with projections which can interact with cut-outs or holes made in that face of the outer flange which faces towards the vessel wall. Such projections interacting with cut-outs or holes can improve anchoring.

Especially when, in the case of an ETS anastomotic, the graft vessel to be joined has a diameter which is larger than that of the target vessel—which is generally the case when joining a by-pass vessel to the coronary artery, the so-called distal anastomotic—it is advantageous according to a second aspect of the invention, which essentially is independent of the first aspect, if the bottom rim of the tubular body has an essentially oval or elliptical contour. When fitted on the target vessel, the longitudinal axis of the oval or ellipse will then extend essentially parallel to the longitudinal direction of the target vessel. According to the second aspect of the invention, a bottom rim of the tubular body having an essentially oval or elliptical contour is, however, also advantageous if the graft vessel has to be joined to the target vessel at an angle, as can be the case with an ETS anastomotic irrespective of the relationship between graft vessel and target vessel diameter, and can also be the case with an ETE or STS anastomotic. Such an anastomotic device of oval or elliptical design can also very readily be produced by modifying in this sense anastomotic devices known from the prior art.

According to a third aspect of the invention, which can be used independently of the first and/or second aspect but highly advantageously can also be used in combination with the first and/or second aspect, the invention relates to an anastomotic device for joining a graft vessel to a target vessel at an opening present therein, such as, in particular, an opening present in the wall thereof, comprising an outer flange which is intended to be brought into contact, by means of an outer flange contact surface, with the outside of the wall of the target vessel around the opening, characterised in that the outer flange contact surface is of cylindrically curved construction, preferably with a radius of curvature which is equal to or approximately equal to the external circumferential radius of the target vessel at the location of the opening. By making the outer flange contact surface of cylindrically curved construction, constriction of the target vessel at the location of and as a consequence of the anastomotic device is reduced or, if the radius of curvature is equal to or approximately equal to the external radius of the target vessel at the location of the opening, even completely prevented. Reduction of the constriction or complete preclusion of the constriction of the target vessel at the location of the anastomotic device has the advantage that the flow through the target vessel at the location of the anastomotic device is impeded to a lesser extent or is even not impeded at all. Such a cylindrically curved outer flange can, in particular, be advantageously used in the case of an STS or ETS anastomotic. It will be clear that a cylindrically shaped outer flange of this type can also very readily be achieved by modifying in this sense anastomotic devices known from the prior art.

In order further to counteract compression of the target vessel and, consequently, thus constriction of the target vessel at the location of the anastomotic device, it is particularly advantageous, in the case of said third aspect according to the invention, if the outer flange contact surface has the shape of, essentially, a cylinder sector which extends over at most 180°. Extension of the cylinder sector over more than 180° is not entirely precluded, but this makes fitting the anastomotic device on the target vessel, and fixing it thereto, somewhat more complicated since in this case either the target vessel has to be pinched together to some extent in order to be able to place this in the cylinder sector section of the outer flange or the cylinder sector section must be constructed such that it is either flexible or can be bent open. The cylinder sector will preferably extend over a range of 150° to 180°. What can be achieved by the use of such a cylinder sector section for the outer flange contact surface is that the outer flange is able to bear on tissue that is located around the target vessel, in particular tissue in which the target vessel is embedded. The tissue located on/over the target vessel and, if necessary, the tissue alongside the target vessel is removed or pushed aside to a small extent, after which the outer flange is then able to sink into the tissue and is able to bear thereon. It should be clear that constriction of the target vessel is reliably extensively prevented/avoided by this means.

For applications in coronary artery surgery the radius of curvature of the outer flange contact surface will, according to an advantageous embodiment of the invention, be in the range from 0.5 to 1.25 mm for distal anastomotic at the location of the coronary artery, (which here in general has a diameter of 1 to 2.5 mm). In the case of a proximal anastomotic at the aorta ascendens, which then in general has a diameter of 3 to 5 cm at this location, the radius of curvature of the outer flange contact surface will be in the range from 15 to 25 mm.

In order to achieve a uniform clamping force around the opening in the target vessel with an anastomotic device having a curved outer flange contact surface, it is advantageous according to the invention if, when using an inner flange having an interrupted or uninterrupted inner flange contact surface, the inner flange is of cylindrically curved construction with a radius of curvature which is equal to or approximately equal to the internal circumferential radius of the target vessel at the location of the opening; or is equal to or approximately equal to the radius of curvature of the outer flange contact surface.

For coronary artery surgery the radius of curvature of the inner flange contact surface will then, corresponding to the radius of curvature of the outer flange contact surface, preferably be in the range from 0.5 to 1.25 mm in the case of distal anastomotic with the coronary artery or in the range from 15 to 25 mm in the case of proximal anastomotic with the aorta.

In the case of proximal aorta anastomotic, the aorta ascendens displays (slight) curvature towards the left-hand side of the patient (towards the right-hand side from the surgeon's view) at the location of the anastomotic. In order to improve the join even further it can thus be advantageous if the outer flange contact surface, and optionally also the inner flange, is constructed not only with the abovementioned cylindrical shape (in the anteroposterior direction of the patient, the so-called sagittal plane) in the longitudinal direction of the aorta (or outer flange), but also concave in the case of the outer flange or convex in the case of the inner flange.

In order fully to complete the join between the target vessel and the graft vessel it is advantageous according to the invention if the anastomotic device further comprises coupling means for fixing the free end of the graft vessel (or target vessel) to the anastomotic device, for example the tubular body thereof, or for fixing a first anastomotic device to a second anastomotic device. With this arrangement, fixing of the graft vessel (target vessel) could take place directly at, for example, the outer flange or at a component that has been made in one piece with the tubular body and/or the outer flange. Such a component made in one piece with the tubular body can optionally be located inside the tubular body. However, fixing can also take place to a separate, independent component which, after the graft vessel has been fixed thereto, is coupled to the anastomotic device.

According to a farther advantageous embodiment of the invention, with this arrangement the coupling means comprise an accessory which has a passage for the graft vessel and can be at least partially inserted in the tubular body, the tubular body and/or the accessory preferably being provided with a stop which is arranged such that it prevents the accessory from being able to protrude beyond the bottom rim of the tubular body. If the coupling means comprise a separate accessory which can be inserted in the tubular body, fixing of the graft vessel to the anastomotic device outside the body is relatively simplified, the anastomotic device itself can be of relatively simpler construction and fixing of the anastomotic device to the target vessel can be achieved relatively easily since, if appropriate, it is easy here to use an instrument that can be placed through the anastomotic device into the target vessel and can then be removed so as, finally, actually to produce the join of the graft vessel on the target vessel by means of said accessory.

The coupling means can thus comprise a separate component that is fixed to the anastomotic device, for example to the tubular body, for example after the tubular body has first been fixed by means of inner flange and outer flange to the target vessel, but the coupling means can also have been formed in one piece with the anastomotic device, for example with the tubular body, in which case in general the graft vessel will first be joined to the tubular body and only then will the tubular body be fixed to the target vessel by means of the inner flange and outer flange. In this latter case joining of the tubular body to the graft vessel can take place outside the patient's body and in the former case joining of the graft vessel to the separate auxiliary coupling piece can take place outside the patient's body.

In order to be able to join the graft vessel without constricting this, or possibly with minimal constriction, by means of the anastomotic device, it is advantageous if the coupling means have a series of passages for suture which are arranged around the periphery of the tubular body or the separate accessory and pass through the tubular body or the separate auxiliary coupling piece, the passages preferably having a diameter of approximately 0.5 to 1.5 mm. Said passages will run essentially radially with respect to the graft vessel or the tubular body or the auxiliary coupling piece.

According to an advantageous embodiment of the invention, the coupling means comprise a flexible and/or resilient ring which is sized such that the connection end of the graft vessel can be inserted through it and wrapped back over it, a peripheral groove, which opens inwards and in which the ring, together with part of the folded-back connection end of the graft vessel, can be accommodated, preferably in a tight-fitting manner, being provided in an internal peripheral surface of the anastomotic device, preferably of the tubular body thereof. Such a flexible and/or resilient ring in combination with a peripheral groove makes it possible for the anastomotic device to be fixed to the target vessel first and for the graft vessel, after it has been provided with the flexible and/or resilient ring, then to be joined to the anastomotic device by deforming the flexible and/or resilient ring and inserting this in the anastomotic device and accommodating it in the peripheral groove, preferably in a tight-fitting manner. With this arrangement pulling free of the graft vessel can advantageously be counteracted by allowing the peripheral groove to open at a downward slope into the target vessel. According to an advantageous embodiment, manipulation of the flexible and/or resilient ring is facilitated if two or more rod-shaped parts are fixed to the ring, which rod-shaped parts are essentially at right angles to the ring, extend in the axial direction thereof and are fixed at the other ends to a flexible sleeve. By pinching or otherwise deforming the flexible sleeve, the ring can then be deformed via the rod-shaped parts and manipulated in order to be able to insert it in the anastomotic device and fit it in the peripheral groove.

According to a farther advantageous embodiment of the invention, the coupling means can comprise an outwardly tapering tube, which is sized such that the connection end of the graft vessel can be inserted through it and folded back over it, and a clamping ring which can be slid over the tube from the narrow end, with the folded-back part of the graft vessel lying between the ring and the tube, until the ring is firmly clamped on the tube, with the folded-back part of the graft vessel lying between ring and tube. Coupling means of this type can be produced very simply and are also easy to use. With this arrangement, the clamping ring and/or the outwardly tapering tube can have been provided with locking means in order to be able to lock these to the remainder of the anastomotic device to produce the join of the graft vessel on the target vessel.

The coupling means as described in particular in claims 15–23 can optionally also be used entirely independently of aspects 1 to 4 according to the invention.

If, in the case of the coupling means, a distinction is made between, on the one hand, coupling means with which separate, additional coupling accessories are not needed and, on the other hand, coupling means with which separate, additional coupling accessories are needed, the following can then be pointed out. Coupling means with which additional coupling accessories are not needed can, for example, comprise a ring of holes running all round the anastomotic device, which can advantageously be used in ETS and ETE anastomoses in particular. Such a ring of holes can be made in an upright ring-like or cylindrical part, which is placed on the outside of the outer flange, and can be regarded as the tubular body. In the case of coupling means without additional accessories consideration can also be given to coupling means for coupling two anastomotic devices to one another, for example by providing one with an internal groove in which an external rib of the other fits, as can be useful in the case of STS anastomoses and also ETS and ETE anastomoses. As will be seen from the description of the figures, diverse embodiments are conceivable here. In the case of coupling means with which one or more separate, additional coupling accessories are needed, consideration can be given, in a simple form, for example, to a straight tube through which the graft vessel is inserted and is folded back around it by its end, after which a ligature or tie wrap is applied from the outside, after which the whole can then be fitted in the tubular body and fixed, for example by clamping or any form of coupling, such as a mechanism involving serrations, or barbs. However, other possibilities are also not only conceivable but also realistic. For example, consideration can be given to the use of a flexible ring around the end of the graft vessel, which ring, in turn, can be accommodated in a groove or slit made in the anastomotic device, or to a tube through which a graft vessel is inserted and wrapped round at one end so as to be clamped on the tube by means of a slidable ring, which whole can then be fitted and fixed in the anastomotic device.

In order further to improve the join of the graft vessel to the target vessel, in particular in the case of an ETS anastomotic when the target vessel is the coronary artery, it is advantageous according to a fourth aspect of the invention if the passage through the tubular body and/or the passage through the accessory which can be inserted through the latter and/or the coupling means are equipped such that the graft vessel is joined at an angle which is not equal to 90° and is preferably less than 70°, such as, for example, 60°, 45° or 30°, with respect to the target vessel. What this will amount to in the case of the passage through the tubular body being suitably equipped and/or the passage through the accessory which is insertable in the tubular body being suitably equipped is that the respective passage is positioned at an angle with respect to the outer flange. In use, the respective passage will then accommodate the end of the graft vessel to be joined or be located in the extension thereof. Said fourth aspect can be used either independently of the first and/or second and/or third aspect of the invention, for example with the prior art such as, for example, WO 96/25886, or in combination with the first and/or second and/or third aspect according to this invention. The advantage of an oblique join of the graft vessel on the target vessel is that in the case of a heart by-pass the effect of the pericardium or other structures, such as the lungs, in the vicinity thereof on the graft vessel is reduced. Specifically, in the case of an (approximately) right angle join such an effect can easily lead to bending or kinking of the graft vessel or compression of the graft vessel or target vessel and thus impede the blood flow.

In the case of an oblique join of the graft vessel to the target vessel, the anastomotic device, or at least one or more parts thereof located transversely on the target vessel, will have an essentially oval or elliptical shape/contour. In the case of the join of a graft vessel to a coronary artery said oval or elliptical shape/contour will be much more pronounced than in the case of the join of a graft vessel to the aorta.

In order to counteract rejection phenomena it is advantageous according to the invention if the anastomotic device according to the invention is made of or coated with a material that is inert with respect to the human or animal body, such as types of high grade stainless steel, titanium and Teflon-like plastics or other plastics, which may or may not be based on Teflon.

In order to counteract clotting phenomena it is advantageous according to the invention if the anastomotic device according to the invention, or at least the inner flange and/or arms of the anastomotic device and/or those parts of the anastomotic device which come into contact with blood are coated with materials which counteract blood clotting. Materials of this type which prevent or counteract blood clotting are known per se. In this context consideration can be given to a carbon coating, a heparin coating or a so-called negative charge. An example of a material which inhibits blood clotting is silicon carbon.

However, it is not precluded that in practice the invention is used in combination with the use of rejection inhibitors and/or anticoagulants (thrombosis inhibitors) by the patient.

The present invention will now be explained in more detail below with reference to illustrative embodiments shown in the drawing. In the drawing:

FIG. 1 shows, diagrammatically, a graft vessel (by-pass) between the aorta ascendens and the coronary artery of the heart, around a constriction/blockage in said coronary artery;

FIG. 2 shows, diagrammatically and in a partially exposed perspective view, an anastomotic device according to the invention which is made up of three components, for ETS joining of, in particular, a graft vessel to a coronary artery, in which the coupling (or fixing) between the (separate) coupling piece, with the graft vessel joined thereto, and the remainder of the anastomotic device at the location of the opening in the coronary artery is shown in an exploded view;

FIG. 11b shows, in cross-section, a detail from FIG. 11a;

Figure 14:
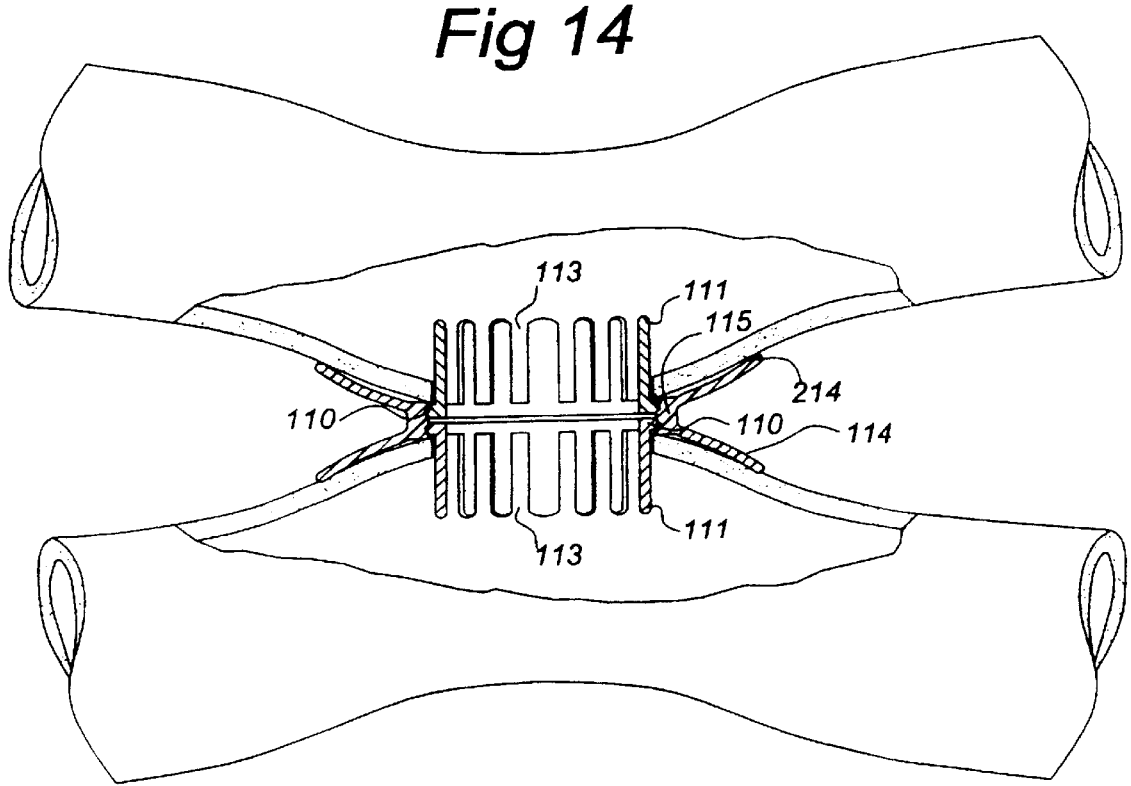
Figure 15:
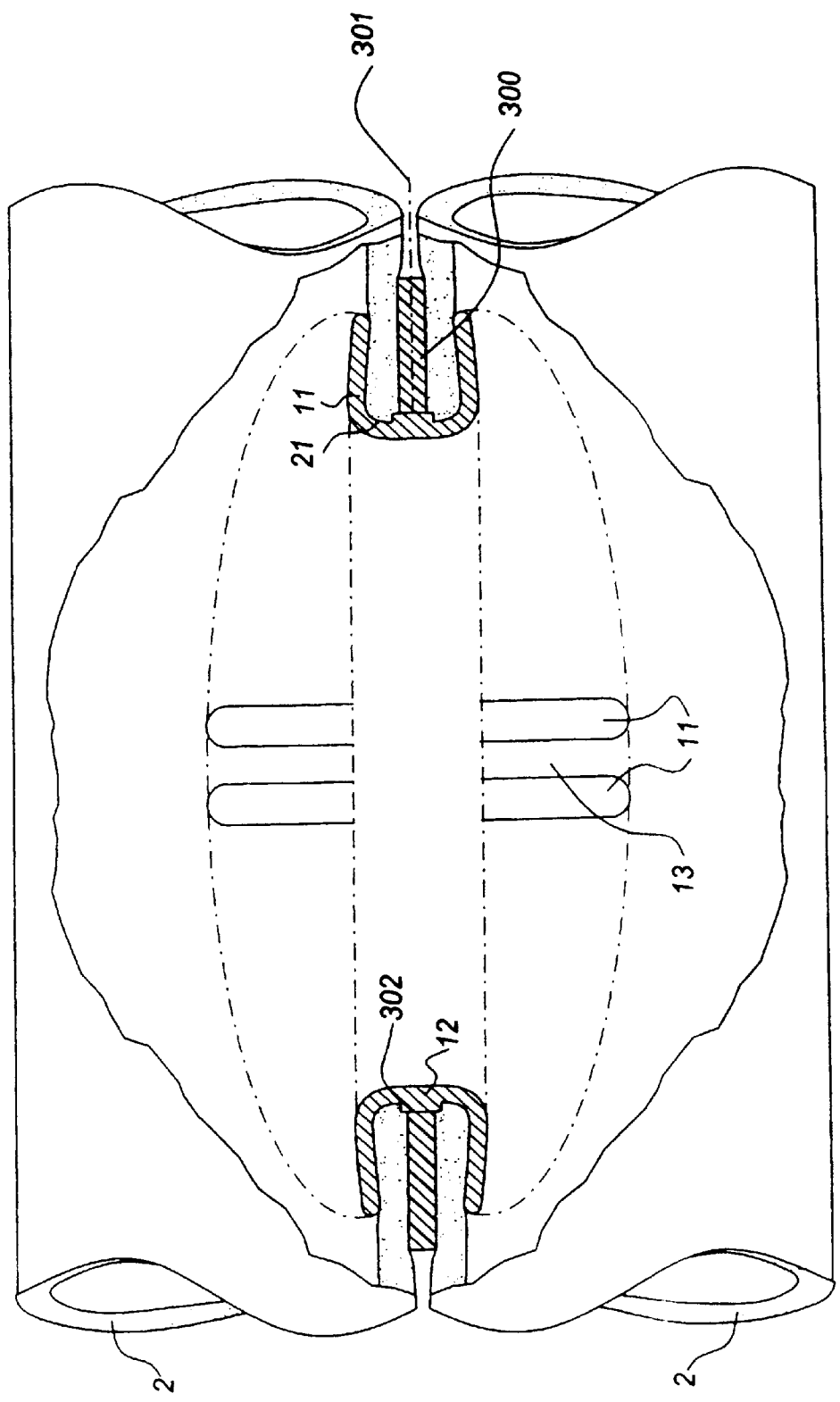
Figure 16:
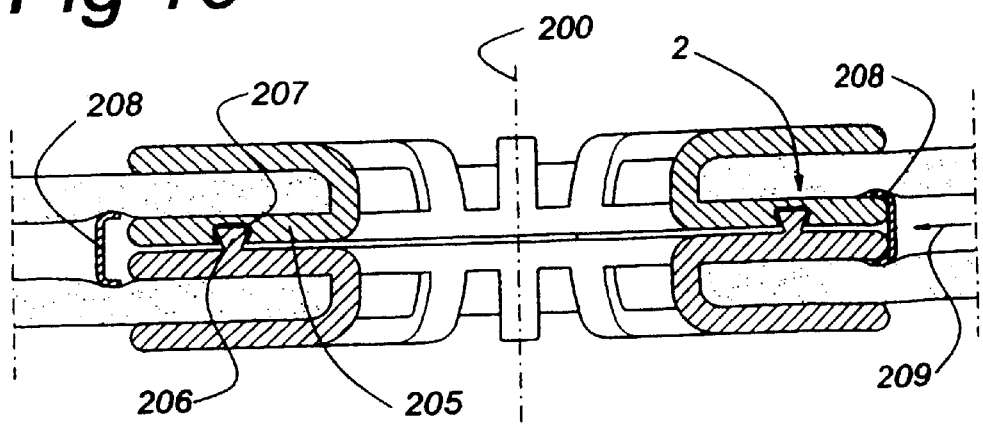
Figure 18:
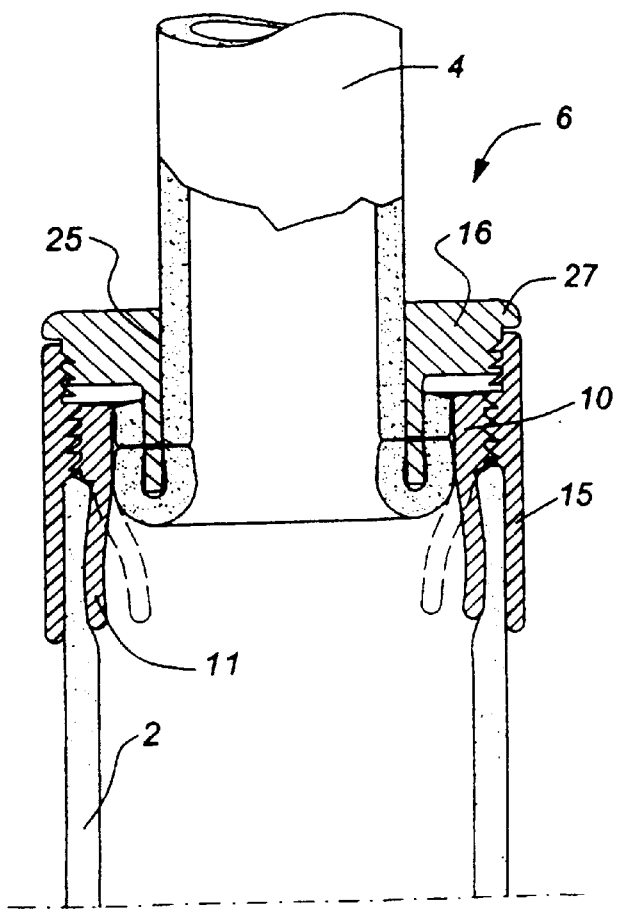
Figure 17:
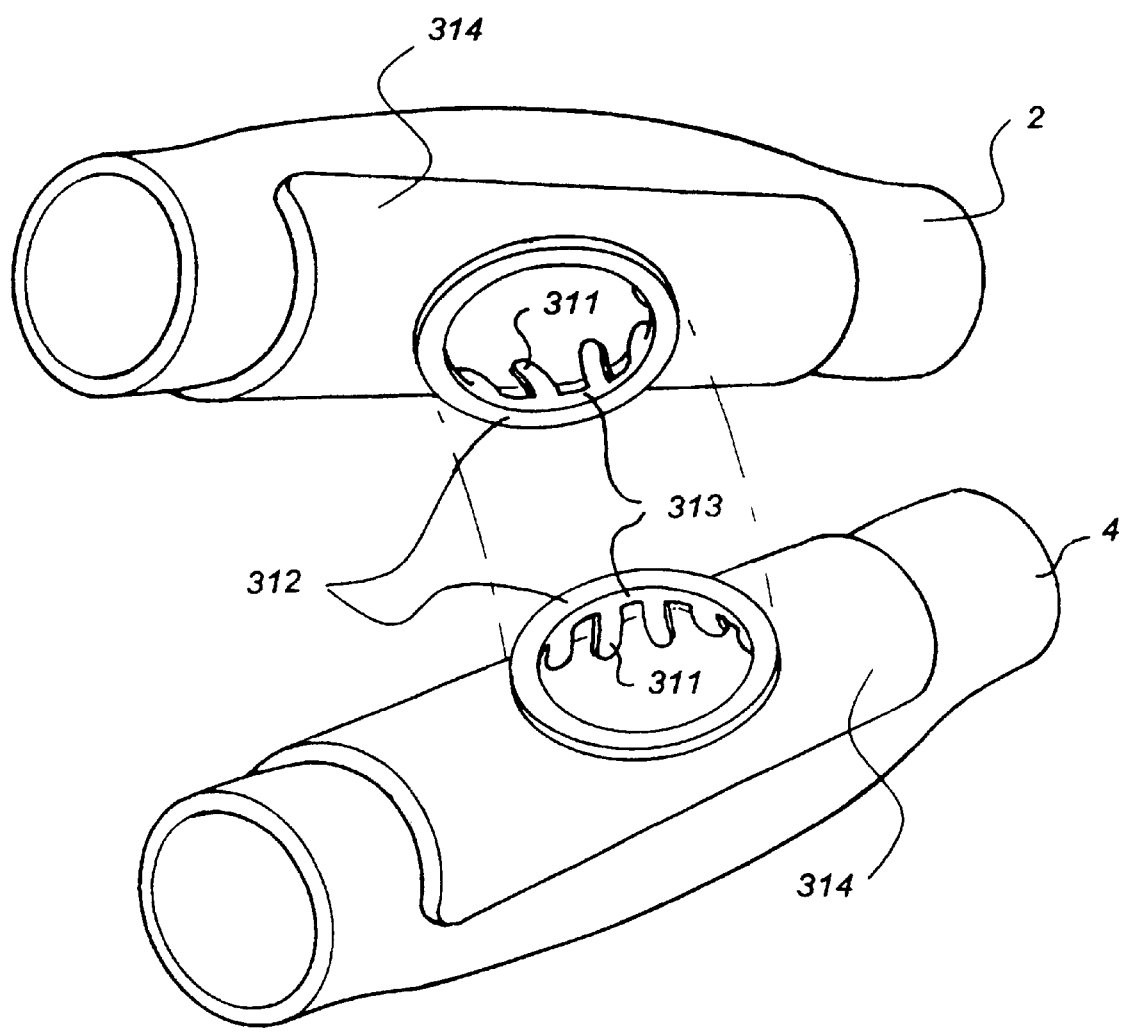
Figure 19:
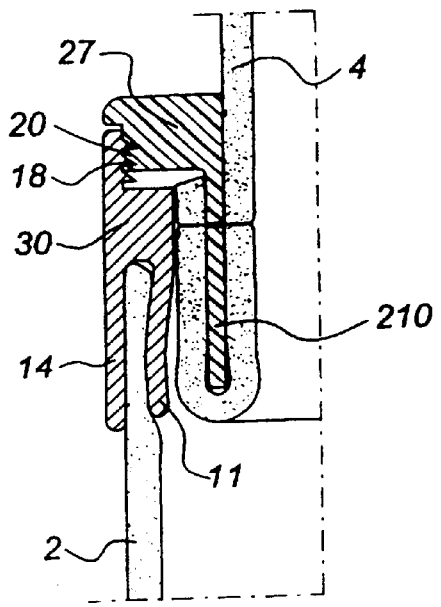
Figure 20:
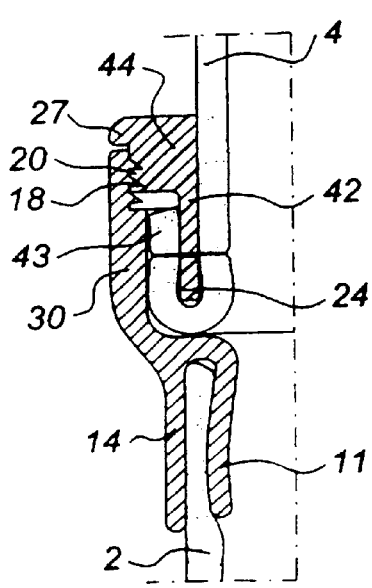
Figure 21:
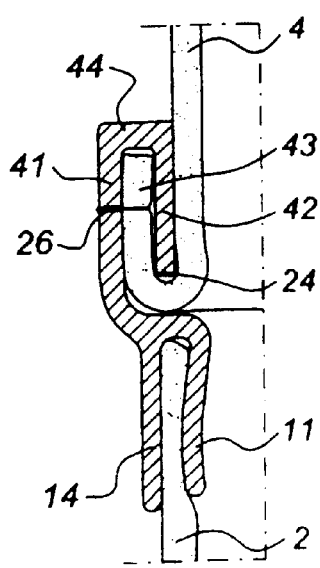
Figure 22:
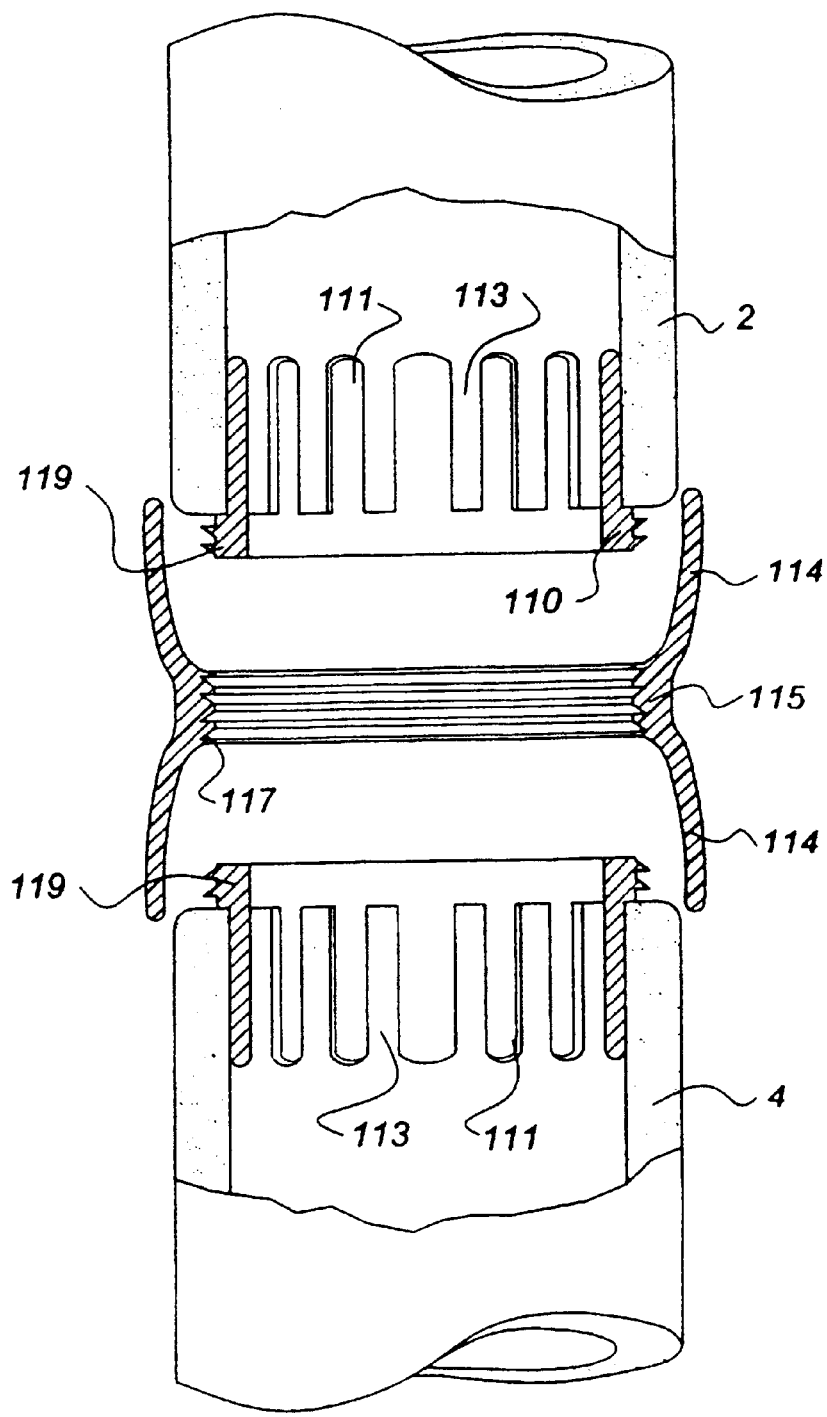

FIGS. 13A to F show, highly diagrammatically, six anastomoses, specifically two examples of each of the three types of anastomoses;

FIG. 14 shows a diagrammatic cross-sectional view, partially in front view, of an STS anastomotic device according to the invention;

FIG. 15 shows a diagrammatic cross-sectional view, partially in front view, of a second embodiment of an STS anastomotic device according to the invention;

FIG. 16 shows, diagrammatically, a detail of a cross-sectional view of a third embodiment of an STS anastomotic device according to the invention;

FIG. 17 shows a diagrammatic, perspective view of an STS anastomotic device according to the invention;

FIG. 18 shows a diagrammatic cross-sectional view, partially in front view, of a first embodiment of an ETS anastomotic device according to the invention;

FIG. 19 shows in diagrammatic cross-section a detail of a second embodiment of an ETE anastomotic device according to the invention;

FIG. 20 shows a detail of a longitudinal section of a third embodiment of an ETE anastomotic device according to the invention;

FIG. 21 shows a detail of a longitudinal sectional view of a fourth embodiment of an ETE anastomotic device according to the invention;

FIG. 22 shows a cross-sectional view, partially in front view, of a fifth embodiment of an ETE anastomotic device according to the invention;

With regard to the figures discussed above it is pointed out that these are all diagrammatic.

Figure 1:
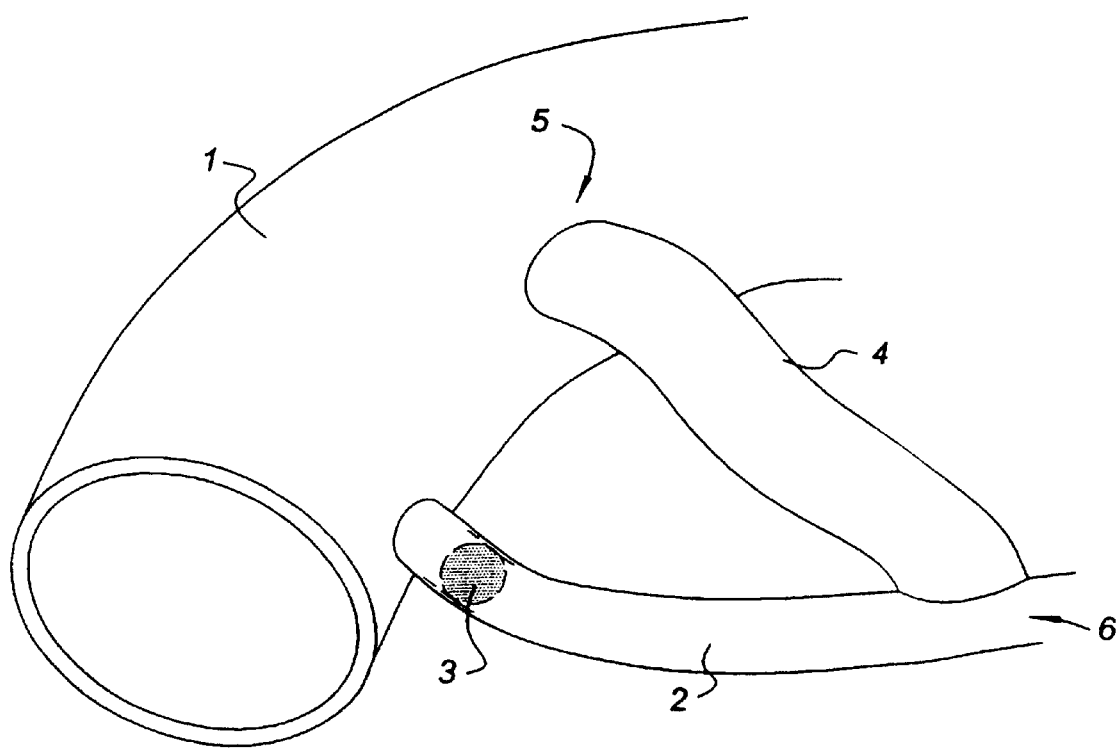

FIG. 1 shows, as an example of an application for an anastomotic device according to the invention, highly diagrammatically, an aorta 1, a coronary artery 2 with a blockage 3 and a graft vessel 4, which is also termed a by-pass. The graft vessel 4 is frequently a vein taken from the leg or (rarely) the arm or an artery from behind the sternum, a stomach artery, an artery from the abdominal wall or an artery from the arm. However, in practice other human vessels, animal vessels or artificial vessels can also be used and can also be employed with the aid of the invention in the same way as the veins and arteries mentioned above. Such a vein, artery or vessel in general has a diameter and vessel wall thickness which are greater than those of the coronary artery 2 and smaller than the diameter and vessel wall thickness of the aorta. The diameter of the aorta in such cases generally varies from about 3 to 5 cm. The diameter of the coronary artery, in which the blockage 3 is located, generally varies from approximately 1 to 2.5 mm. Conventionally up to now, the by-pass, both for the proximal anastomotic 5 with the aorta 1 and for the distal anastomotic 6 with the coronary artery 2, is attached to the aorta or, respectively, coronary artery by means of suturing by hand. Since the diameter of the graft vessel 4 is greater than that of the coronary artery 2, in the case of the distal anastomotic the coronary artery 2 can be provided with a lengthwise incision having a length approximately equal to the width of the pinched-flat distal end of the graft vessel 4, or the graft vessel can be cut off at an angle immediately. In this position the graft vessel 4 is then stitched firmly, in the somewhat pinched-flat or ellipsoidal state, to the coronary artery.

On the basis of FIG. 1 it will be clear that the term target vessel must be understood to cover both an aorta and a coronary artery or possibly another blood vessel, or more generally a hollow tubular organ, such as a urethra or Fallopian tube.

Figure 2:
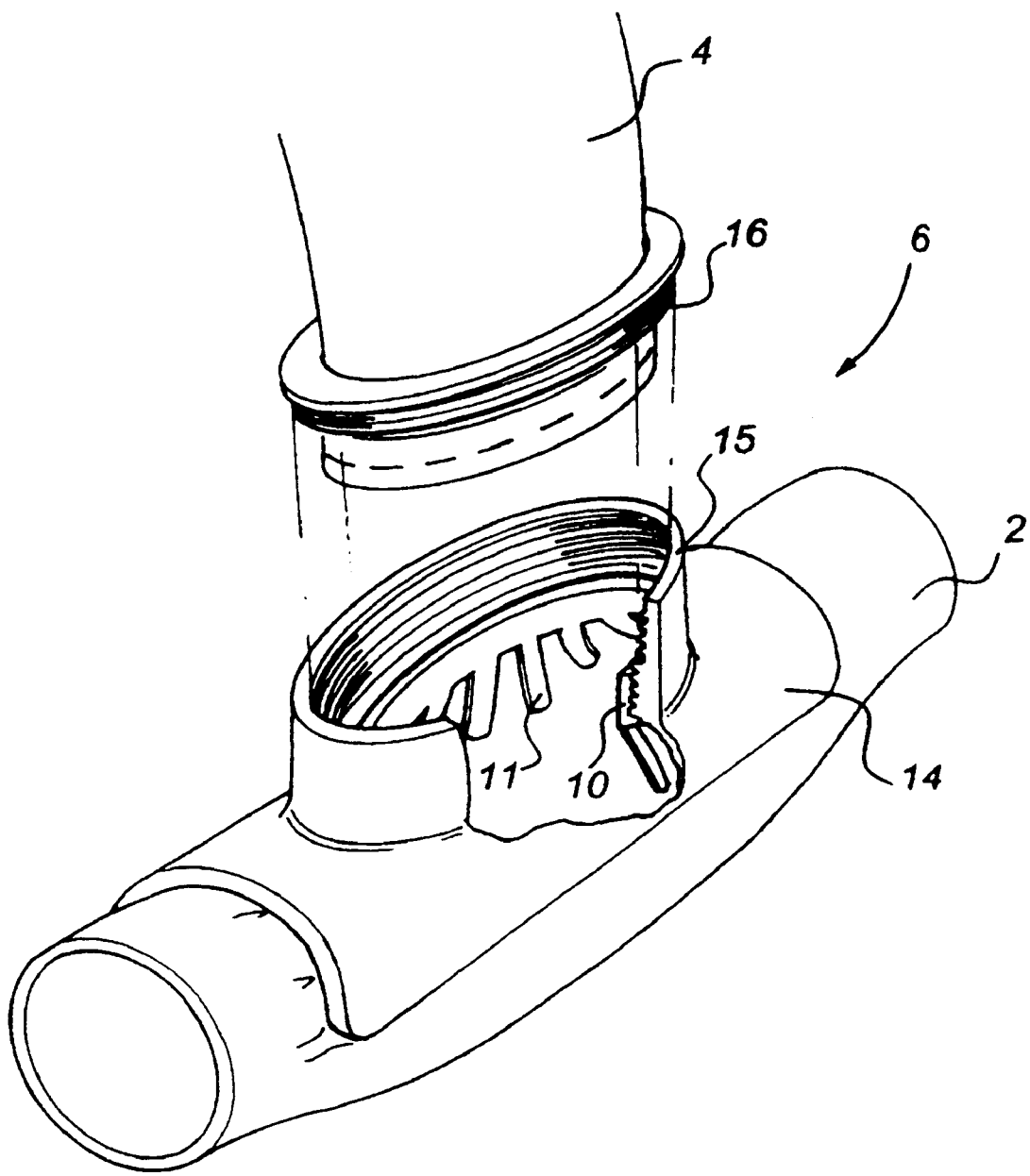
Figure 3:
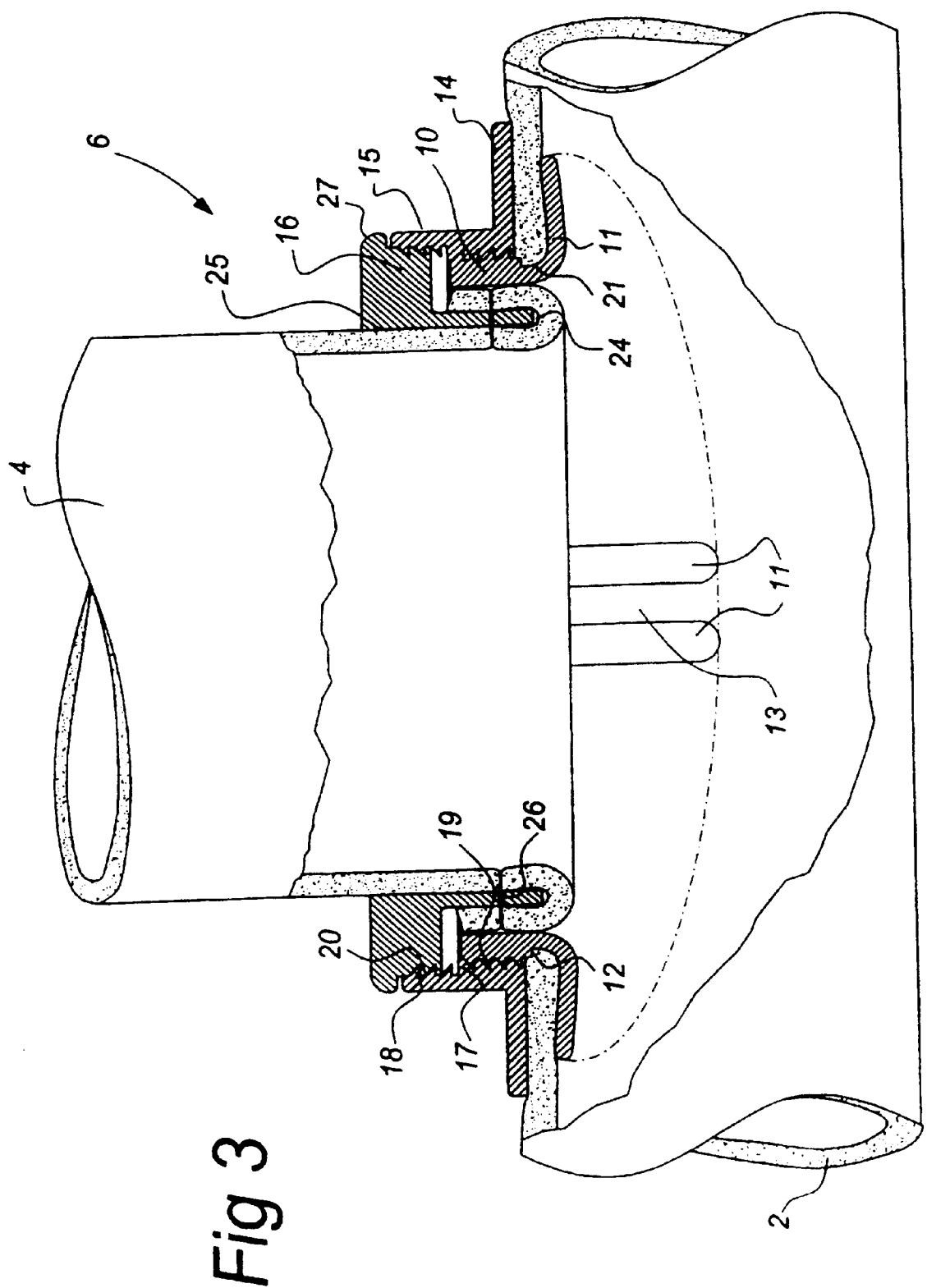
FIG. 3 shows a longitudinal sectional view of the three-part ETS anastomotic device according to FIG. 2.
Figure 4:
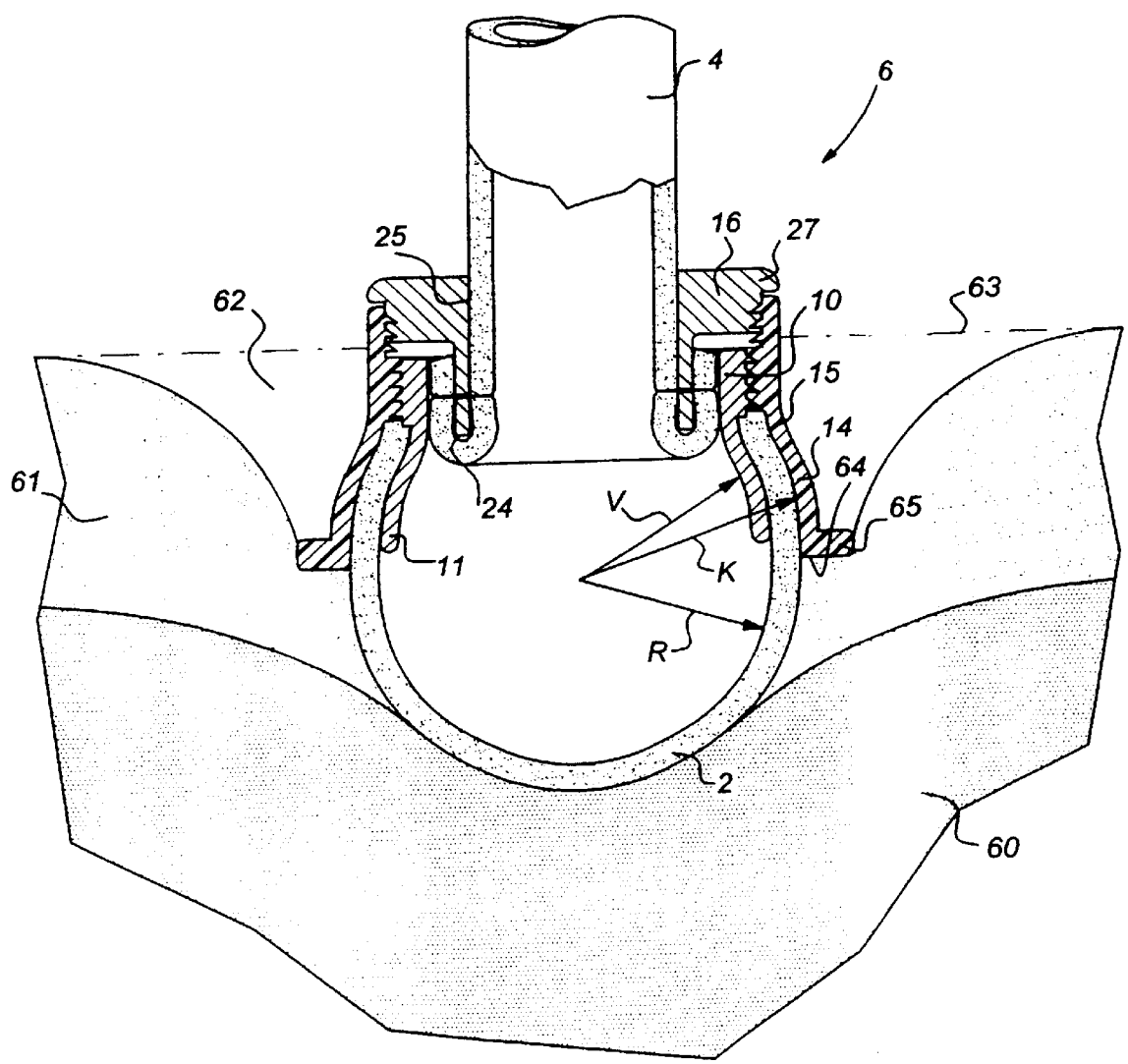
FIG. 4 shows a cross-sectional view of the three-part ETS anastomotic device according to FIGS. 2 and 3.

FIGS. 2, 3, 4 and 5 show, diagrammatically, embodiments of a three-part ETS anastomotic device according to the invention. FIGS. 2, 3 and 4 show essentially the same embodiments in, respectively, perspective view, partially exploded view, longitudinal sectional view and cross-sectional view. The surrounding tissue shown in FIG. 4 is not shown in FIGS. 2 and 3. FIGS. 2, 3 and 4 relate to a distal anastomotic, which, in accordance with the reference in FIG. 1, is indicated by 6, whilst FIG. 5 relates to a proximal anastomotic, which, in accordance with FIG. 1, is indicated by 5. The important difference between, on the one hand, the anastomotic device in FIGS. 2–4 for the distal anastomotic 6 and, on the other hand, the anastomotic device in FIG. 5 for the proximal anastomotic is that in the case of the proximal anastomotic the anastomotic device can be of essentially cylindrical construction whereas in the case of the distal anastomotic the anastomotic device is essentially in general of oval/elliptical construction. The reference numerals used for the aorta, the coronary artery and the graft vessel in FIGS. 2–5 and, incidentally, also in the other figures are the same as those used in FIG. 1.

The anastomotic device according to FIGS. 2, 3 and 4 consists of a tubular body 10 having arms 11 formed at a bottom rim 12, which arms 11 are separated from one another by notches 13 which have been made in a finger-like pattern distributed around the periphery of the tubular body 10. The anastomotic device further comprises, as a separate component, an outer flange 14 arranged at one end of a cylindrical bush 15 and a coupling accessory 16.

Figure 5:
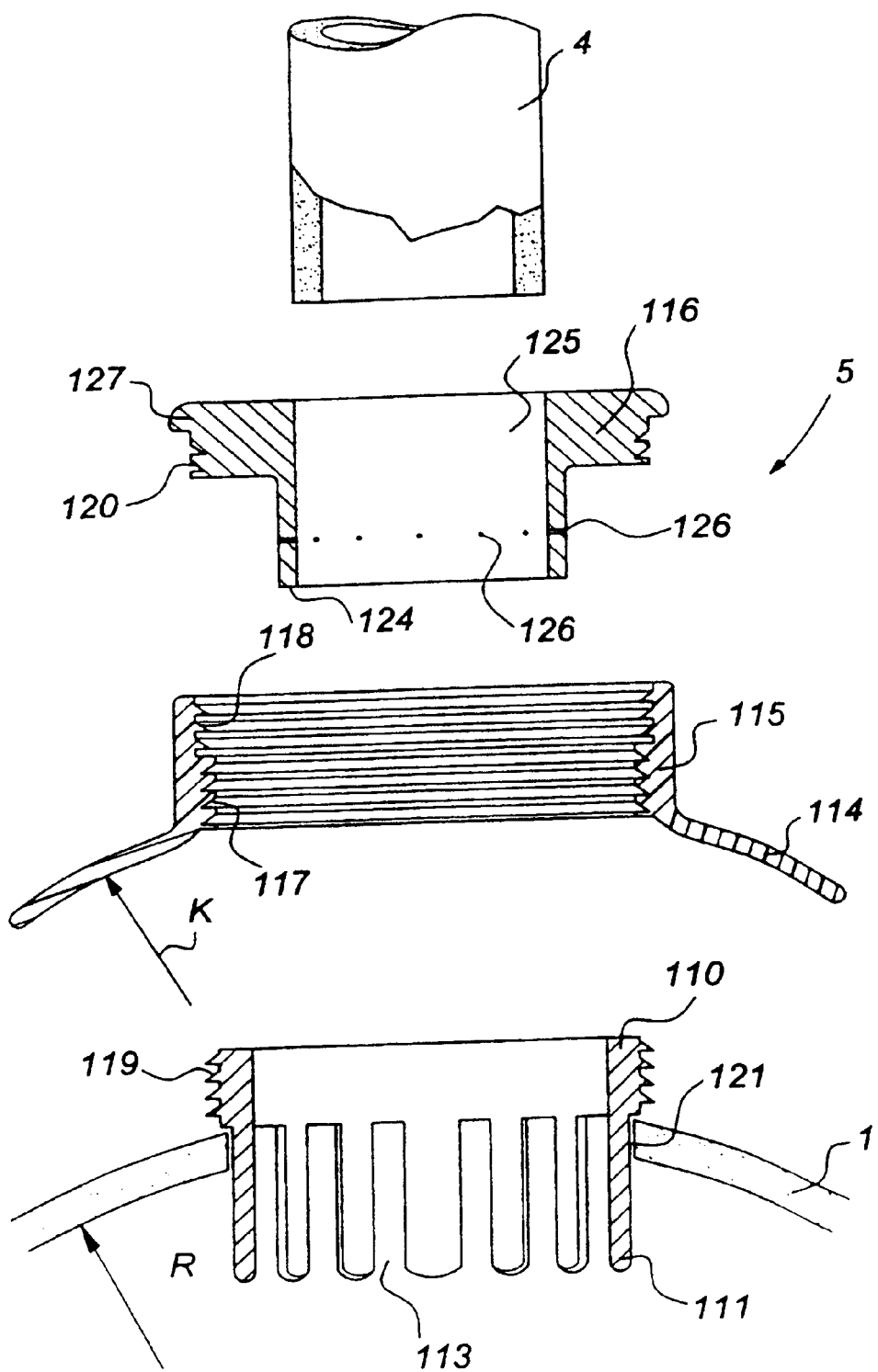
FIG. 5 shows a cross-sectional view of a three-part ETS anastomotic device with components shown in exploded view, which anastomotic device is very similar to the anastomotic device in FIGS. 2, 3 and 4 but differs from the latter in that this is an anastomotic device for, in particular, joining a graft vessel to an aorta.

The anastomotic device in FIG. 5 is of corresponding construction and the same reference numerals raised by 100 have been used for the corresponding parts, this also being the case with regard to corresponding components which are yet to be discussed.

The bush 15, 115 is provided on its inside with two sets of serrated profiling facing in opposing directions, a lower serrated profiling 17, 117 and an upper serrated profiling 18, 118. The lower serrated profiling 17, 117 can interact with the serrated profiling 19, 119 on the outside of the tubular body 10, 110 and the upper serrated profiling 18, 118 can interact with the serrated profiling 20, 120 on the coupling piece 16, 116. The respective serrated profiles make it possible, successively, first to insert the tubular body 10, 110 by its arms through an opening 21, 121 made in the wall of the target vessel 2, 1, then to release the fixing of the pretensioned state of the arms 11, 111 by heating, after which the arms 11, 111, as a consequence of the memory properties of the arm material, are able to bend (back) outwards from the position shown in FIG. 5 into the position shown in FIGS. 2, 3 and 4 until they come into contact with the inside of the wall of the target vessel 2, 1 around the opening 21, 121, then to bring the outer flange 14, 114 into contact with the outside of the wall of the target vessel 2, 1 around the opening 21, 121 by pushing the bush 15, 115 over the tubular body 10, 110 and bringing the serrated profiles 19, 119 and 20, 120 into engagement with one another and sliding them relative to one another until an adequate clamping force has been produced between the outer flange 14, 114 and the arms 11, 111 forming an inner flange, and then inserting the coupling piece 16, 116, with graft vessel 4 already fitted thereon, in the bush 15, 115, the serrated profiles 20, 120 and 18, 118 then engaging in one another. The depth to which coupling piece 16, 116 can be inserted in bush 15, 115 is delimited by the stop 27, 127 made on coupling piece 16, 116, which stop 27, 127 in the lowest position comes into contact with the top rim of the bush 15, 115. In this way it can be ensured that the bottom end 24, 124 of the coupling piece 16, 116 cannot be inserted too deeply into the tubular body 10, 110 and thus protrude into the target vessel 2, 1. Restriction of the insertion depth can also be implemented in other ways, for example by forming a stop on the inside of the tubular body 10 at the level of the bottom rim 12 thereof.

Joining of the graft vessel 4 to the coupling piece 16, 116 can be achieved by inserting the graft vessel 4 through the passage 25, 125 in the coupling piece 16, 116 and then firmly attaching the graft vessel 4 to the coupling piece 16, 116 by means of suturing, making use of radial suture passages 26, 126 in the coupling piece 16, 116. It is optionally possible during this operation to wrap the graft vessel 4 around the bottom end 24, 124 of the coupling piece 16, 116, as is shown in FIGS. 2–5, which has the advantage that contact between blood and the coupling piece and also contact between blood and the front end edge face of the graft vessel are avoided as far as possible. A further advantage is that with wrapping round the suture join between the graft vessel 4 and the coupling piece 16, 116 is then more robust as a consequence of the larger number of points of engagement of the suture on the graft vessel. However, it is not absolutely essential to wrap the graft vessel 4 around the bottom end 24, 124 of the coupling piece 16, 116 as can be seen above from FIGS. 7c–e or will be seen.

The outer flange contact surface located on the inside of the outer flange 14 has a radius of curvature K which is essentially equal to the radius of curvature R of the target vessel 2, 1. The arms 11, 111, which in the free position shown in FIGS. 2–4 form the so-called inner flange (which can thus be a discontinuous inner flange), preferably have, in their free position, a shape/location corresponding to the radius of curvature K of the outer flange, such that the arms 11, 111 run essentially parallel to the outer flange 14, 114, so that the clamping force between the arms 11, 111 in the free position and outer flange 14, 114 is essentially equal everywhere.

Because the notches 13 between the arms 11 extend as far as the tubular body 10 it is possible to achieve a situation where the top/outside, as seen in FIGS. 2–5, of the arms 11, in the free position, is in virtually flat contact with the inside of the wall of the target vessel 2, 1. In the assembled position, the notches then extend as far as or beyond (above) the outer flange.

FIG. 4 further illustrates, highly diagrammatically, the advantage of an outer flange 14 in the form of essentially a half cylinder, or at least an outer flange of which one section is in the shape of a half cylinder. Specifically, the outer flange could be of rounded construction with a section that is essentially in the shape of a half cylinder only in the middle. In the case of such a rounding, the outer flange 14 is then somewhat saddle-shaped with a cylindrical mid section.

FIG. 4 shows, in cross-sectional view, a coronary artery 2 which is embedded in fatty tissue 61 on the heart 60; at least prior to fitting the anastomotic device the coronary artery 2 was, as is shown by the shadow line 63, as it were virtually completely or completely embedded in the fatty tissue 61. Before fitting the anastomotic device, the fatty tissue must be scraped away at 62 in order to make the coronary artery 22 accessible. The outer flange 14 is now able to bear by its longitudinal edges 64, which optionally are provided with bearing ribs 65 (shown in FIG. 4 and not shown in FIGS. 2 and 3), on the fatty tissue 61 and closing of the coronary artery 2 at the location of the anastomotic device by compression is thus counteracted. Said closing by compression could easily occur since in practice there is also further tissue outside the fatty tissue 61, in FIG. 4 at the top thereof, that can exert pressure on the anastomotic device and/or the graft vessel 4 and thus close the coronary artery 2, which has been exposed as a result of scraping away fatty tissue at 62, by compression at the location of the anastomotic device. Furthermore, the coronary artery can also be pressed closed by the weight of the anastomotic device itself.

In FIG. 4 it is further illustrated that the outside surface of the arms 11 comes into contact with the inside of the wall of the target vessel 2 and that said arms thus come to lie parallel to the outer flange 14 and thus, viewed in a plane transverse to the target vessel, run in a curve according to an arc of a circle V, which arc of a circle V as a consequence of the relatively small wall thickness of the target vessel 2 is essentially equal to the radius of curvature K.

As will be clear from the above, the anastomotic device in FIGS. 2–4 is essentially identical to the anastomotic device in FIG. 5, except that those parts of the anastomotic device in FIGS. 2–4 which are essentially at right angles to the target vessel 2 have an oval/elliptical shape, as is clearly visible in FIG. 2 in particular. Such an oval/elliptical shape makes it possible for a graft vessel 4 having a relatively larger diameter to be joined laterally to a target vessel 2 having a relatively smaller diameter (compared with the graft vessel 4). This situation arises in particular in the case of the ETS attachment of a graft vessel 4 to a coronary artery 2. The elliptical/oval shape in the case of the embodiment according to FIGS. 2–4 is thus in particular reflected in the tubular body 10, the bush 15, the coupling piece 16 and in the end of the graft vessel 4 that is to be joined, which does not so much have this shape beforehand but is brought into this shape. In the case of the (proximal) anastomotic device in FIG. 5 the tubular body 110, the bush 115 and the coupling piece 116 are of essentially round shape, that is to say viewed in a plane essentially transverse and horizontal to the plane of the drawing in FIG. 5. However, it must be pointed out that a proximal anastomotic device can also be of oval or elliptical construction, corresponding to the distal anastomotic device in FIGS. 1–4. In the case of the embodiment shown in FIG. 5, the graft vessel 4 when fitted will therefore also have an essentially cylindrical shape. The proximal ETS anastomotic device in FIG. 5 is particularly suitable for joining a vessel 4 of relatively smaller diameter to a vessel 1 having a relatively large diameter compared with the vessel 4.

As a variant of the embodiment according to FIG. 5, it must also be pointed out that it is also very readily possible to opt, instead of for interaction of the serrated profiles 17, 117 of the cylindrical bush 15, 115 and the serrated profiles 20, 120 of the coupling piece 16, 116, for interaction of the serrated profiles 20, 120 of the coupling piece 16, 116 with serrated profiles (not shown) of the tubular body 10, 110, which serrated profiles, which are not shown, would then have to be provided on the inside of the tubular body 10, 110. Of course, in this case the diameter at which the serrated profiles 20, 120 are provided must also be adjusted in more detail.

Figure 6:
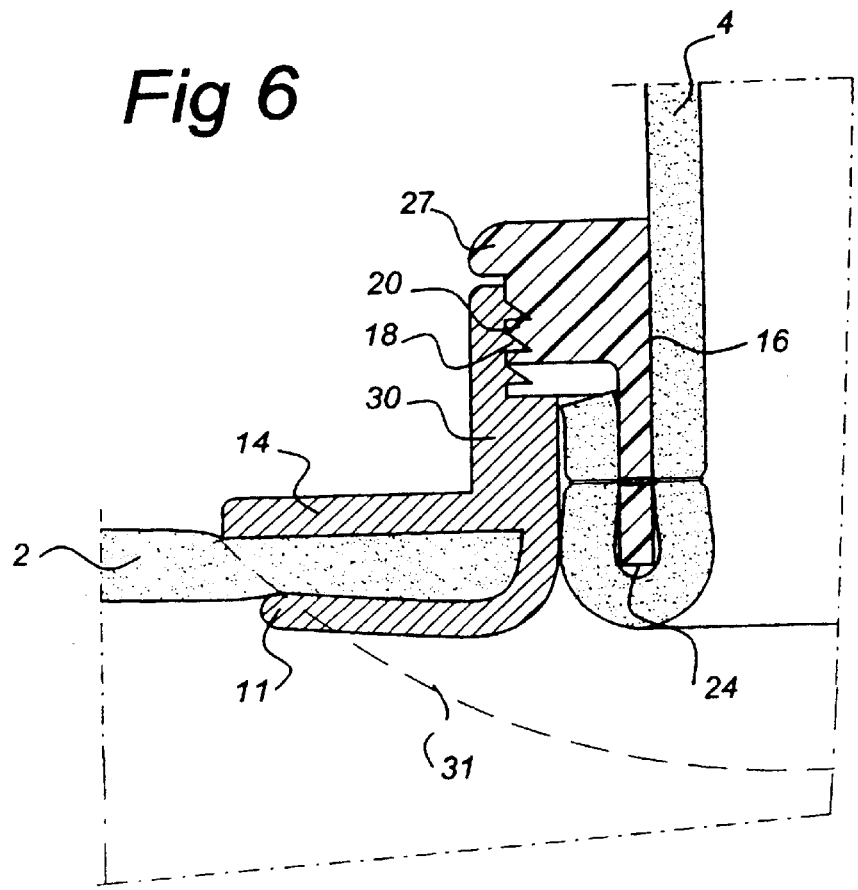
FIG. 6 shows a detail of a longitudinal sectional view essentially corresponding to that in FIG. 3 but now of a two-part ETS anastomotic device according to the invention.

FIG. 6 shows, with respect to the longitudinal direction of the target vessel 2, or if desired 1, a longitudinal section, or at least a detail thereof, of a two-part ETS anastomotic device according to the invention in the fitted position. The essential difference between this ETS anastomotic device and the three-part embodiment in FIGS. 2–5 is that in the case of the two-part embodiment shown in FIG. 6 the tubular body 10 and the bush 15 from the three-part embodiment have been integrated into one piece, the tubular body 30. Since the other components are essentially identical, or at least can be essentially identical, to those in the three-part embodiment according to FIGS. 2–5, the same reference numerals and symbols for corresponding parts have been used for the two-part embodiment in FIG. 6. All of these reference numerals can equally well be read as the same reference numerals increased by 100 (see FIG. 5).

Since the bush 15 and the tubular body 10 of the three-part embodiment have been integrated into one piece in the two-part embodiment, the serrated profiles 17 and 18 can thus be dispensed with in the two-part embodiment.

It is also indicated in FIG. 6, by means of the shadow line 31, that the outer flange 14 is of saddle shape with, viewed in the transverse plane, that is to say a plane perpendicular to the plane of the drawing, a radius of curvature K. The arms 11, in their free position, are also once again essentially parallel to the outer flange 14 and, again viewed in a transverse plane transverse to the plane of the drawing, run with a radius of curvature essentially equal to K. A saddle-shaped outer flange of this type can also be used with the so-called one-part and multi-part embodiments of the anastomotic device.

As a variant of the embodiments according to FIG. 6, it must also be pointed out that it is also very readily possible to implement a two-part embodiment with which the outer flange forms part of a separate component, the first component, and that the coupling piece 16 and the tubular body 10 have been integrated into one piece, the second component. In contrast to the two-part embodiment according to FIG. 6, there is then no need for a stop 27 which forms a limit for the extent to which the bottom edge 24 of the coupling piece 16 can protrude into the target vessel. After all, the coupling piece 16 and the tubular body 10 have then been integrated into a one-part whole, the positioning of the bottom edge 24 of the coupling piece with respect to the remainder of this component then also being specified in advance at the design stage.

Such a variant of the two-part embodiment in which the outer flange 14 forms a separate component that is independent of the remainder is, for example, very simple to implement by providing the tubular body 10 according to the embodiment according to FIGS. 2 and 3 with serrated profiling on the outside and reducing the diameter of the coupling piece 16 so that the latter fits inside the tubular body 10 and can be made in one piece with the latter or joined in one piece with the latter.

Figure 7A:
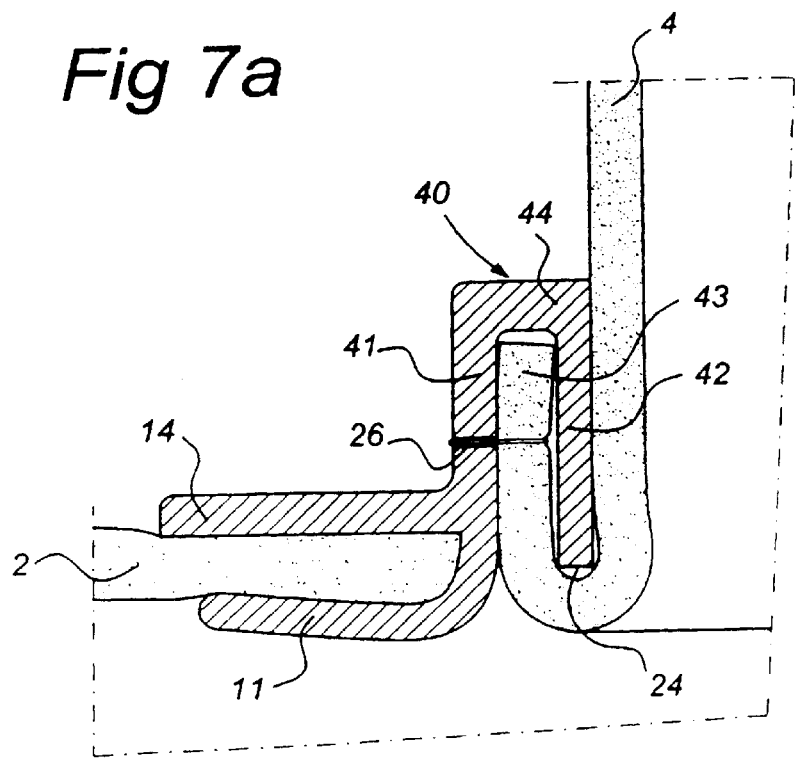
FIGS. 7a to 7e show five detail views corresponding to that in FIG. 6, but each showing a different embodiment of a one-part ETS anastomotic device according to the invention.

FIG. 7a shows, viewed in the longitudinal direction of the target vessel 2, or if desired 1, a longitudinal section, or at least a detail thereof, of a one-part ETS anastomotic device according to the invention in the fitted position. The difference between this anastomotic device and the two-part embodiment in FIG. 6 is that the accessory 16 is now integrated with the tubular body 30 to form one piece, that is to say the tubular body 40. The difference compared with the three-part embodiment in FIGS. 2–5 is that the tubular body 10, the bush 15 and the accessory 16 have been integrated to form one piece, that is to say the tubular body 40. As a consequence of the integration of the accessory 16 with the tubular body it is possible in the case of the one-part embodiment, as will be clear, compared with the two-part embodiment according to FIG. 6 to dispense with the upper serrated profiling 18 and the serrated profiling 20 and compared with the three-part embodiment to dispense with all serrated profiles.

Since in other respects the components of the one-part embodiment according to FIG. 7a are essentially identical, or at least can be identical, to those in the two-part and three-part embodiments, the same reference numerals/symbols have been used for these and these components require no further explanation.

The one-part anastomotic device 40 according to FIG. 7a essentially consists of an outer tubular component 41 and a inner tubular component 42 with a slit opening towards the bottom between them, in which slit the folded-back end section 43 of the graft vessel 4 can be accommodated. Said folded-back section 43 of the graft vessel 4 can then be fixed in place by suturing via radial suture holes 26 made in the outer tubular component 41.

Figure 7B:
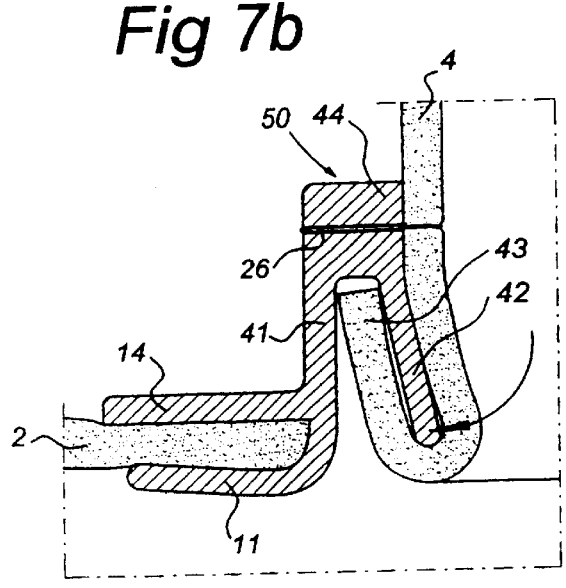

FIG. 7b shows a one-part ETS anastomotic device 50 in a view corresponding to that in FIG. 7a. Said one-part anastomotic device 50 differs from the one-part anastomotic device 40 in FIG. 7a essentially in the sense that the suture holes 26 have been made through the connecting part 44 that joins the outer tubular component 41 and the inner tubular component 42 to one another. The bottom section of the inner tubular component 42 can be bent somewhat inwards with respect to the tubular body 50 as a whole in order to facilitate inserting the folded-back section 43 of the graft vessel 4 between them, after which said component 42 can be bent in accordance with the arrow in the direction of the outer tubular component 41 in order to clamp the folded-back section 43 between the components 41 and 42. Said bending back of the component 42 will preferably be carried out mechanically. The method of clamping the folded-back edge section 43 by bending back the component 42 in accordance with the arrow 7b can also be used in the case of the embodiment according to FIG. 7a.

Figure 7C:
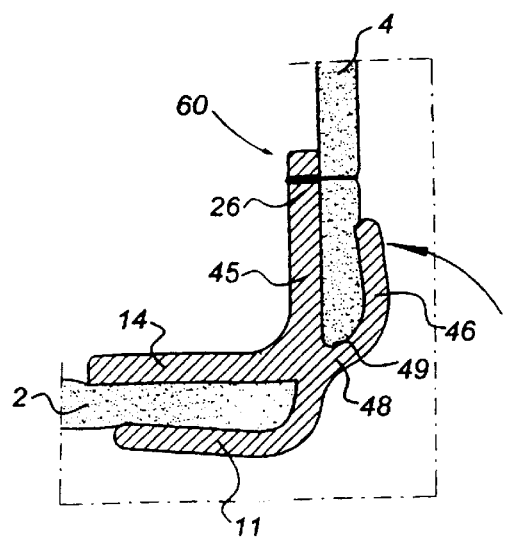

FIG. 7c shows yet a further embodiment of a one-part ETS anastomotic device 60. Said one-part ETS anastomotic device 60 is, as such, again similar to the one-part ETS anastomotic devices 40 and 50 in FIGS. 7a and 7b. The major difference is that here the end of the graft vessel 4 is not folded back but is directly sutured to a tubular component 45 by means of suture passages 26 and is clamped at the bottom end by means of lips 46 which are bendable in accordance with the arrow. Support ribs 47 (see FIG. 7d and FIG. 7e), on which the front end 49 of graft vessel 4 bears in order to prevent it coming into contact with blood, can have been formed between the roots 48 of adjoining lips in the peripheral direction.

As can be illustrated with reference to FIGS. 7a–7c, attachment of the graft vessel to the anastomotic device can also be effected by clamping the end of the graft vessel in place. In the case of FIGS. 7a and 7b the end 43 of the graft vessel is then, optionally employing the first aspect of the invention, clamped between the components 41 and 42 of the anastomotic device and in the case of FIG. 7c clamping of the end of the graft vessel then takes place between the components 45 and 46. Fixing in place by means of suturing, as is shown in FIGS. 7a–7c, can then optionally be dispensed with entirely, which implies that the suture holes 26 can thus be omitted completely. In order to improve such clamping of the end of the graft vessel it can be advantageous to provide the components 41 and/or 42 in the case of FIGS. 7a and 7b or components 45 and 46 in the case of FIG. 7c with a roughening, profiling, projection, etc. on that side thereof which faces towards the clamped end section of the graft vessel, in order, as it were, to anchor the end of the graft vessel. In this context it is optionally possible to provide a projection on one of the clamping components, the end of which projection is, in the clamped position, accommodated in a recess in the opposite clamping component.

Figure 7D:
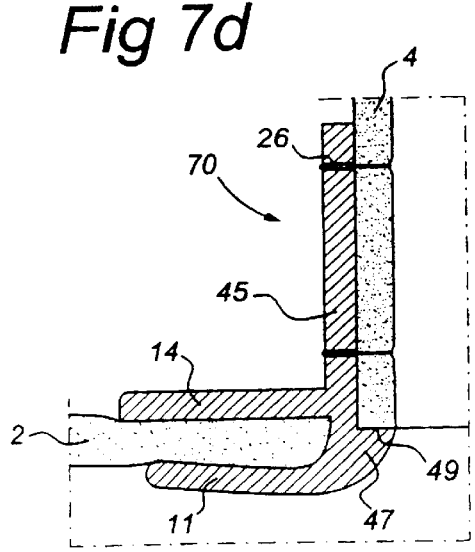

FIGS. 7d shows a further variant of a one-part anastomotic device 70, which shows many similarities with the one-part anastomotic device 60 in FIG. 7c. The difference is that here two rings having suture passages 26, instead of one, as in FIG. 7c and incidentally also in FIGS. 7b, 7a and FIG. 7e, which is still to be discussed, are provided in the cylindrical section 45, viewed in the peripheral direction. Furthermore, the clamping lip 46 has been omitted and, at the location of the root 48, an uninterrupted support rib 47 extending in the peripheral direction on the inside has been provided, the front end 49 of the graft vessel 4 being able to come into contact with said support rib 47 and provide a seal against the blood.

Figure 7E:
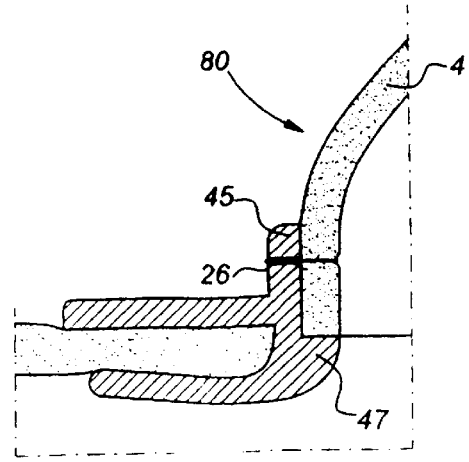

FIG. 7e shows a particularly advantageous embodiment which is a direct variant of the embodiment in FIG. 7d. The anastomotic device 80 shown in FIG. 7e differs from that in FIG. 7d in the sense that the cylindrical section 45 has been made very short and has only one ring having suture passages 26 arranged distributed around the circumference. A major advantage of the anastomotic device 80 is that the graft vessel 4 can relatively easily be joined at an angle with said device, as is also indicated in FIG. 7e.

With regard to the embodiments of the anastomotic devices 70 and 80 in FIGS. 7d and 7e it is also pointed out that the clamping lips 46 in FIG. 7c could be used here as well.

Figure 8:
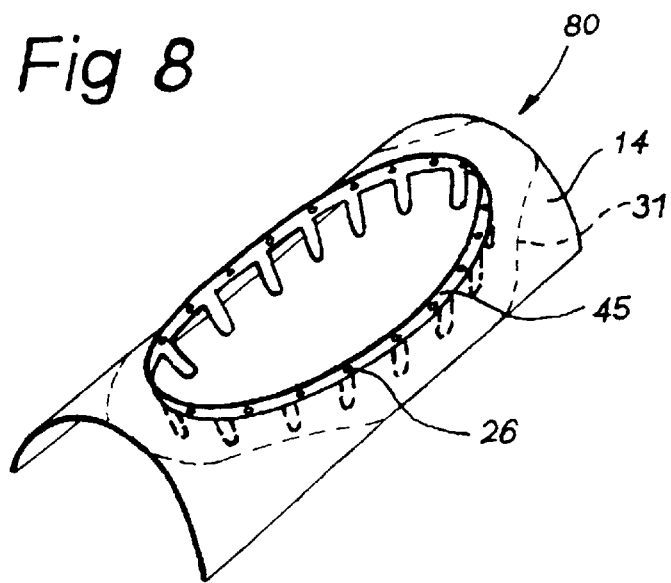
FIG. 8 shows, in accordance with the invention, a diagrammatic, perspective view of one embodiment of a one-part ETS anastomotic device having an upright edge provided with radial passages.

The anastomotic device 80 shown in FIG. 7e as a detail of a longitudinal section is also shown in a perspective view, in the unfitted state with arms 11 still extended, in FIG. 8. In other respects said figure will speak for itself.

With regard to the embodiments of the anastomotic device as shown in FIGS. 6 and 7a–7e and FIG. 8 it is pointed out that the outer flange 14 in these embodiments can have been constructed as is shown by continuous lines in FIG. 8, that is to say as a half cylinder or a cylinder sector extending over approximately 180°. The outer flange 14 can, however, also equally well assume a different shape, such as, for example, a saddle shape, which is shown diagrammatically by broken line 31 in FIG. 8.

It is further pointed out that the anastomotic devices as shown and described with reference to FIGS. 6, 7a–7e and FIG. 8 can also very well be used in accordance with the embodiment outlined in FIG. 5, it then being possible for essentially all components transverse to the target vessel to be constructed with a round periphery.

Incidentally, what has been pointed out in the previous two paragraphs with regard to FIGS. 6, 7a–7e and 8 applies equally well to FIGS. 10, 11a, 11b and 12, which are still to be discussed below, and also to FIGS. 9a and 9b and further figures to be discussed in more detail.

Figure 9A:
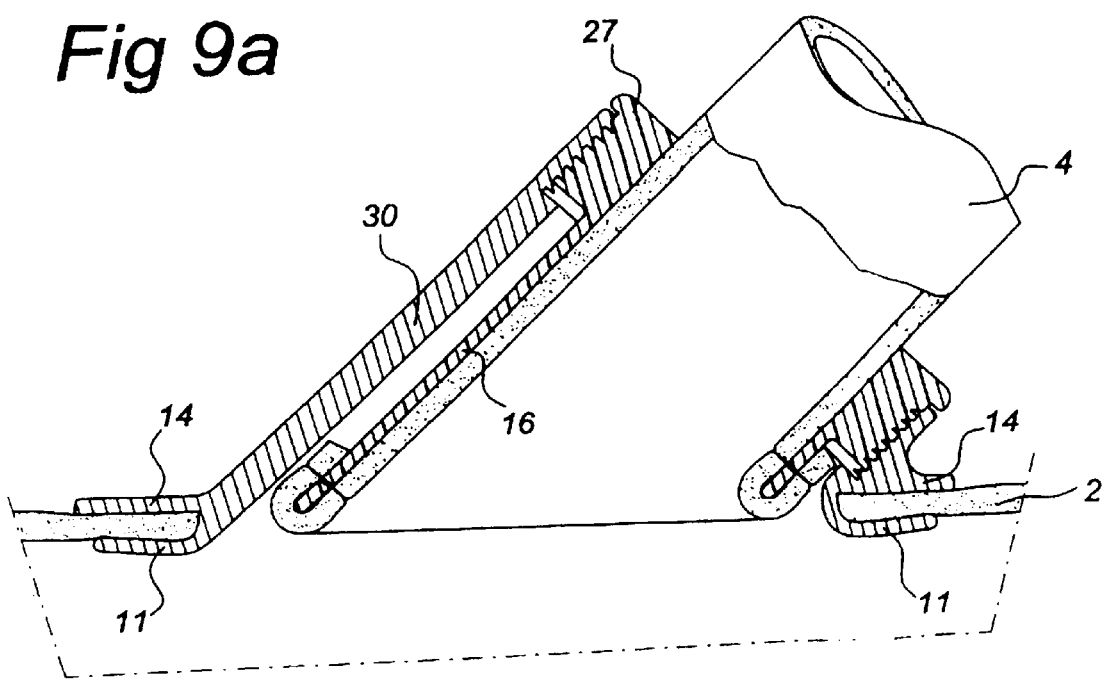
FIGS. 9a and 9b show two variants of a two-part ETS anastomotic device according to the invention having an oblique join.
Figure 9B:
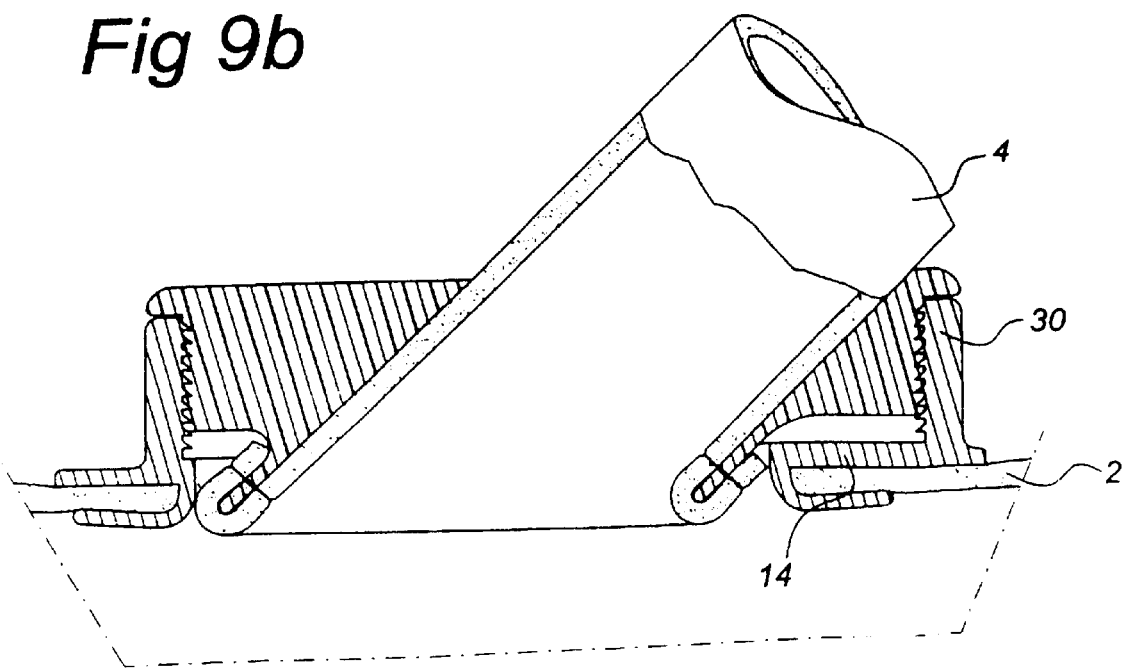

FIGS. 9a and 9b show, diagrammatically, two further embodiments of the ETS anastomotic device according to the invention. These embodiments have been so designed that graft vessel 4 can be joined to the target vessel 2 at an angle of approximately 450. In the case of the embodiment according to FIG. 9a this is achieved by placing the tubular body of the two-part embodiment in FIG. 6 on the outer flange 14 at an angle and placing the tubular body 16 of the coupling piece at a corresponding angle and cutting off at an angle. In the case of the embodiment according to FIG. 9b this is achieved by providing the tubular body 16 with a sloping passage or at least taking the two-part embodiment according to FIG. 6 as the starting point. A further corollary of this is that the outer flange 14 also comes to lie partially within the bush 30. In other respects the embodiments according to FIGS. 9a and 9b are essentially identical to the embodiment according to FIG. 6.

It will furthermore be clear that the oblique joins shown in FIGS. 9a and 9b can also readily be implemented in the case of the one-part and multi-part embodiments which have already been described above and are still to be described, so that it will be clear that the oblique join is also certainly not restricted to the two-part embodiment.

Figure 10A:
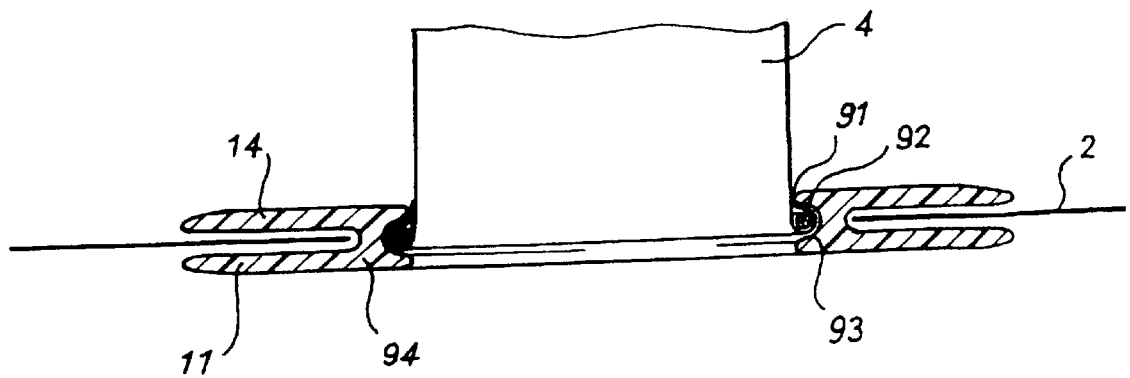
FIG. 10a shows a diagrammatic cross-sectional view of a further embodiment of a two-part ETS anastomotic device according to the invention, showing in particular an embodiment of the coupling means for joining the graft vessel to the tubular body by means of a flexible and/or resilient ring.
Figure 10B:
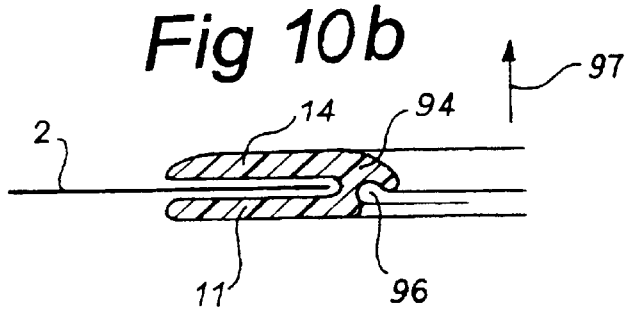
FIG. 10b shows a further alternative embodiment of FIG. 10a of the coupling means for joining the graft vessel to the tubular body.

With reference to FIGS. 10a and 10b a further fixing possibility for attachment of the graft vessel 4 to the anastomotic device according to the invention is shown on the basis of a further embodiment of a two-part anastomotic device which has not yet been described. However, before discussing this method of fixing it is pointed out that, as will also be immediately apparent, this method of fixing can also very readily be used in the case of the two-part and multi-part embodiments of anastomotic devices according to the invention. The bottom end of the graft vessel 4 is folded back around a flexible and/or resilient ring 92 located in the folded-back section 91. The folded-back section 91 is attached to graft vessel 4 in the peripheral direction above the ring 92 by suturing. The anastomotic device is further provided with a groove which opens essentially in the direction in which the wall of the target vessel 2 extends, that is to say a groove 93 that opens inwards with respect to the tubular body 94 of the one-part anastomotic device. By manipulating the graft vessel 4 that has been prepared beforehand and that thus has been folded back and provided with a flexible and/or resilient ring 92 and at the same time pinching the ring 92 together and releasing it again, the ring 92 can be positioned and anchored in the peripheral groove 93. If a suitable material is chosen for the resilient ring 92, a robust and reliable join between the graft vessel 4 and the anastomotic device will also be obtained in this way.

FIG. 10b shows a variant of the embodiment according to FIG. 10a, or at least a detail of such a variant. The difference lies in the fact that the groove 96 (which as far as its function is concerned corresponds to groove 93) has been made such that said groove opens somewhat towards the bottom. This, on the one hand, makes it easier to accommodate the folded-back end of the graft vessel 4 with resilient ring 92 in said groove and, on the other hand, increases the ability of the graft vessel 4 and the target vessel 2 to resist being pulled apart in the direction of arrow 97. For the sake of clarity it is pointed out that in FIG. 10 b the top is the outside of the target vessel 2 and the bottom the inside of target vessel 2.

Figure 11A:
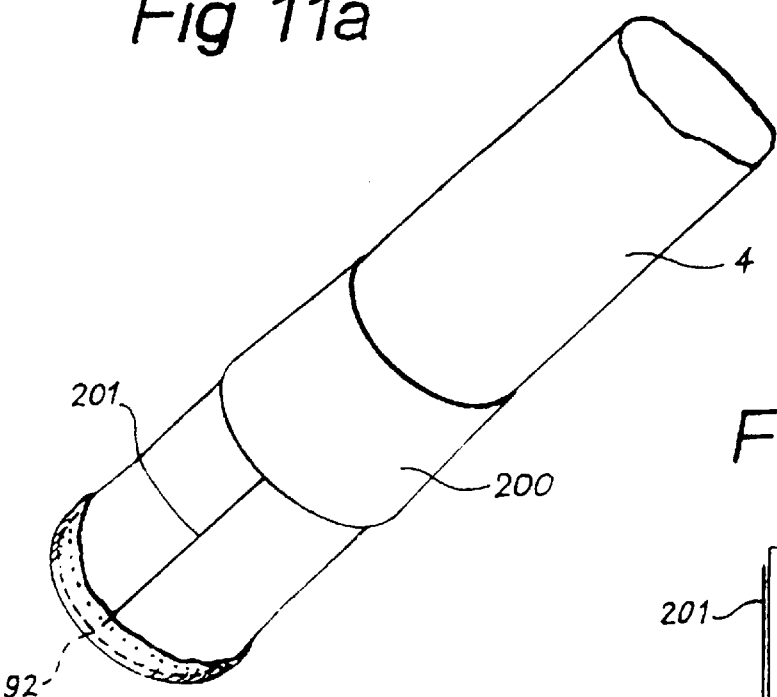
FIG. 11a shows a diagrammatic, perspective view of an assembly aid for coupling the coupling means for fixing the free end of a graft vessel to the tubular body.

FIG. 11a shows a graft vessel 4 with a sleeve 200 around it, which sleeve 200 is provided with at least two rod-shaped parts 201, which join the sleeve 200 to the resilient ring 92. By now pinching the sleeve 200 in one or another direction the ring 92 will also be deformed via the rod-shaped parts 201. It will be clear that this appreciably facilitates manipulation of the graft vessel for the purpose of attaching said graft vessel 4 to the anastomotic device. As soon as graft vessel 4 has been firmly attached to the anastomotic device, the rod-shaped parts 201 can then be cut through, preferably as close as possible to the ring 92, after which the parts of said rod-shaped parts which have been cut off, together with the sleeve 200, can be removed from the graft vessel 4. To this end the sleeve 200 will be cut through in its longitudinal direction or may possibly already have been cut through beforehand so that it can be folded open and removed from the graft vessel 4.

Figure 11B:
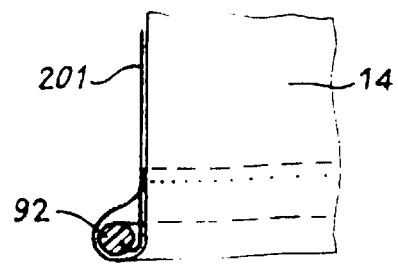

In order to promote good positioning and pressing home of the ring 92 in the peripheral groove 93, 96, it is advantageous if close to ring 92 the rod-shaped parts assume the direction in which the peripheral groove 93, 96 opens or at least are fixed to the ring on that side thereof which faces away from the peripheral groove opening. This is illustrated in FIG. 11b.

The elastic and/or resilient ring 92, as explained with reference to FIGS. 10a, 10b and 11a, is shown as a more or less round ring in FIG. 11a in particular. A round ring of this type can optionally also be used if the anastomotic device, or at least the parts thereof which are transverse to the target vessel, has/have an essentially oval or elliptical shape/contour. In the case of such an essentially oval or elliptical shape/contour of the anastomotic device the ring 92 can, however, advantageously also have a corresponding oval or elliptical shape. Furthermore, it is pointed out that if the graft vessel is cut off at an angle, or at least is folded back at an angle about the ring 92, this type of coupling can also be used for oblique joins.

Figure 12:
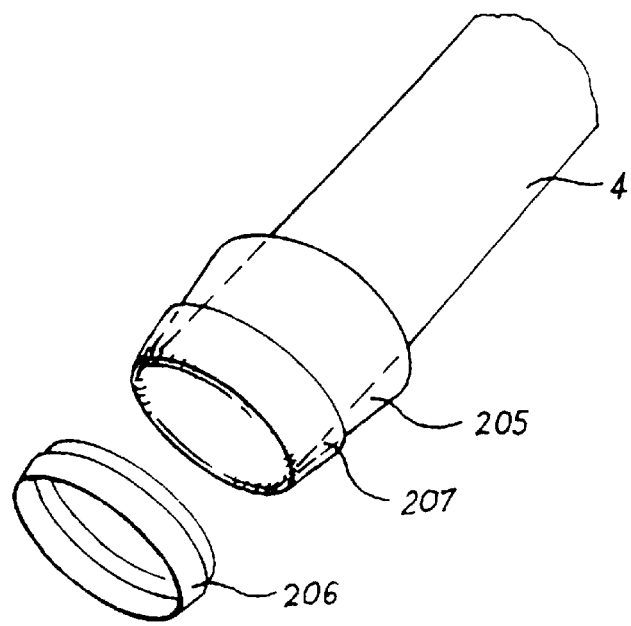
FIG. 12 shows yet a further embodiment of the coupling means for joining the graft vessel to the tubular body by means of a tapering tube.

Yet a further variant of a possible method by which the graft vessel 4 can be attached to the anastomotic device is shown in FIG. 12. With this variant the graft vessel 4 is inserted, by that end thereof which is to be joined through a tube 205 and its end is folded back around said tube 205. The tube 205 will preferably widen in the direction away from the connection end, which, inter alia, facilitates an oblique join of the graft vessel 4 since this then has some freedom of movement in the tube 205. In order to fix the graft vessel 4 in place on the tube 205, a clamping ring 206 is slid over the folded-back end edge section 207 of the graft vessel 4 and clamped firmly, the folded-back wall section 207 of graft vessel 4 then being located between ring 206 and the tube 205. For fixing in the remainder of the anastomotic device, the ring 206 and/or tube 205 can then be provided on their outside with, for example, saw tooth serrations or another form of fixing and anchoring (for example a resilient clamp joint) to the anastomotic device, which are not shown. For instance, consideration can be given, for example, to the saw tooth serrations 6 in FIGS. 2–4 and, furthermore also has a stop edge 27, which is likewise not shown; see, once again, FIGS. 2–4.

Figure 13:
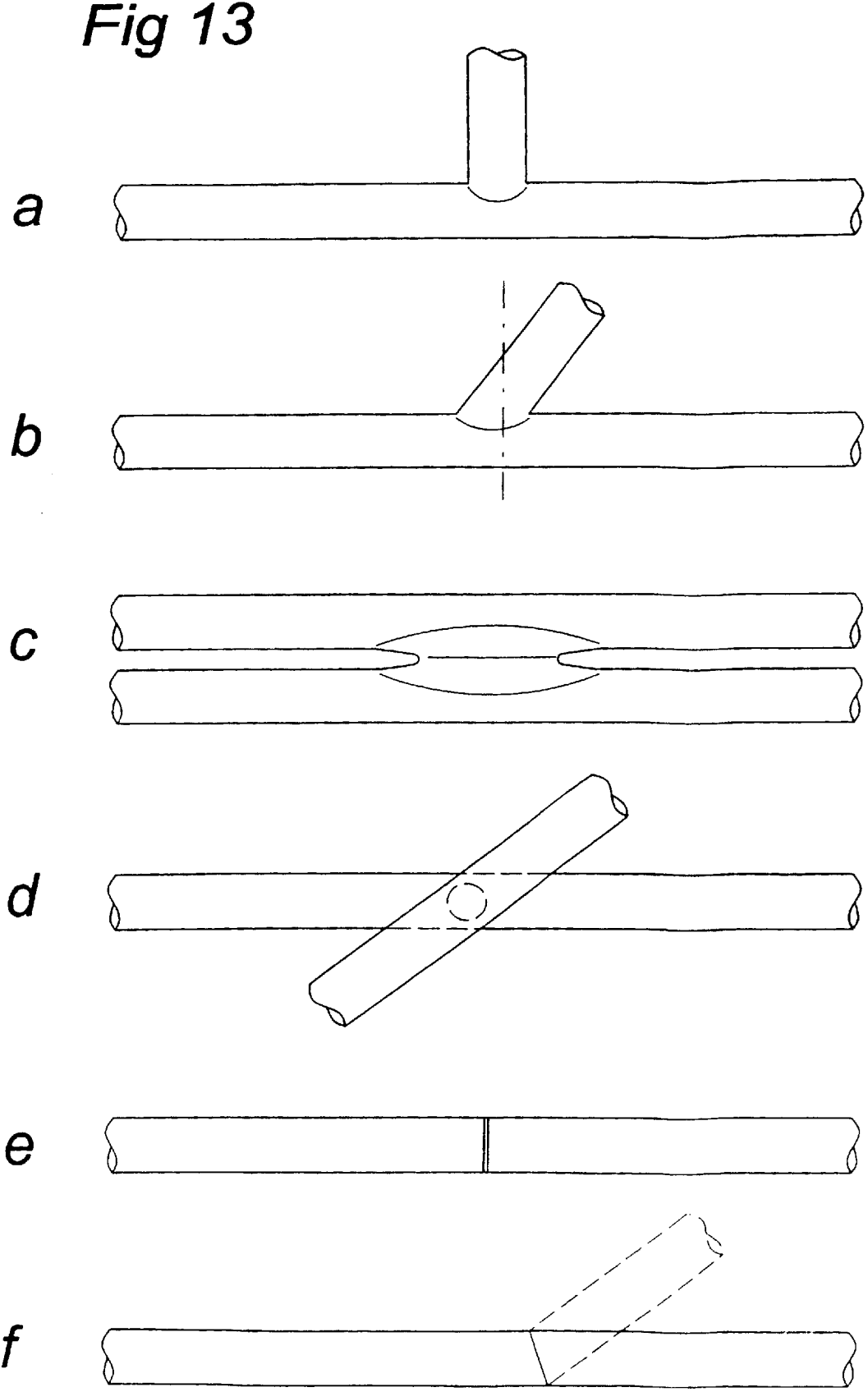

FIG. 13 shows highly diagrammatically, six anastomoses, two of each of the three types. The various aspects of the present invention can be employed with each of these types of anastomoses.

FIG. 13A shows an ETS anastomotic with which one end of the graft vessel is attached at right angles to the target vessel. FIG. 13B also shows an ETS anastomotic, with which, however, the graft vessel is attached to the target vessel at an angle with respect to the latter. If the graft vessel has a diameter which is greater than that of the target vessel, the connection opening will then be elliptical or oval, both in the case of the embodiment according to FIG. 13A and in the case of the embodiment according to FIG. 13B. If the diameter of the graft vessel is smaller than that of the target vessel, the connection opening can then be round or elliptical/oval. This applies both to the anastomotic according to FIG. 13A and to the anastomotic according to FIG. 13B. In the case of the anastomotic according to FIG. 13B, a round connection opening does imply, incidentally, that the graft vessel has a non-circular cross-section in the vicinity of the connection opening, although this non-circular nature can be barely discernible to the eye.

FIGS. 13C and 13D each show a so-called STS anastomotic. The anastomotic in FIG. 13C is an STS anastomotic with which the vessels joined to one another run parallel and in the case of the anastomotic shown in FIG. 13D there are two vessels which cross one another and are joined to one another. The connection opening here can be of round or elliptical shape. The opening will usually be oval/elliptical if graft vessel and target vessel run parallel. In the case of vessels crossing at an angle, the diameter of the opening can usually be no greater than the width/diameter of the smallest vessel, which usually leads to round openings.

FIGS. 13E and 13F each show an ETE anastomotic. In the case of FIG. 13E there are vessels joined to one another in the extension of one another and cut off transversely, in which context in the case of round vessels the connection opening will also be round. In the case of FIG. 13F the ends of the vessels to be joined to one another have each been cut off obliquely. If the oblique angle of the cuts is the same for both vessels and the vessels are positioned in a suitable position with respect to one another, a straight join (shown by continuous lines) is then obtained in the case of FIG. 13F. However, it is also possible to join the vessels to one another at an angle with respect to one another. To illustrate this a vessel is also shown on the right by broken lines. In this case the two vessels can then have been cut off at an angle at their connection end, but it is also possible for one vessel to have been cut off straight, in accordance with FIG. 13E. In the case of the embodiment according to FIG. 13F, the connection opening will in general be of oval or elliptical shape.

FIGS. 14–17 show diagrammatic examples of an STS anastomotic device according to the invention.

The anastomotic device in FIG. 14 is in broad terms comparable to the embodiment in FIG. 5 and essentially consists of two anastomotic device halves. The bottom half is essentially identical to, or at least can be considered as being essentially identical to, the lower tubular body 110 having arms 111 and bush 115 with outer flange component 114. The difference is that the coupling piece 116 has been replaced by the top half of the STS anastomotic device shown in FIG. 14. Said top half likewise consists of a tubular body 110, the upper tubular body (that in essence can be identical to the tubular body 110 of the bottom half), to which the upper outer flange 214 has been fitted by means of external serrations. The upper outer flange 214 has been formed in one piece with the bush 115 and, via said bush 115, also as one piece with the lower outer flange 114. The upper tubular body 110 can be inserted by its bottom end (viewed in accordance with the view in FIG. 14) into the bush 115 in order then to be locked therein by means of the serrations. If the serrations are of suitable construction and the shapes are round it is possible to construct the bottom half and top half such that they can be turned relative to one another.

It will be clear that, if desired, in the case of the embodiment of the STS anastomotic according to FIG. 14 the tubular body 110 of the top half and bottom half and the bush 115 and the outer flanges can also have been constructed in one piece (i.e. as one component). Furthermore, deviating from what is shown in FIG. 14, it is also conceivable to construct the outer flange 214 (or optionally 114) as a component which is separate from bush 115 and the other outer flange 114 (or 214, respectively). Yet a further variant on what is shown in FIG. 14 is that upper tubular body 110 can have been provided with external serrations which engage in internal serrations in lower tubular body 110.

FIG. 15 shows a further variant of an STS anastomotic device according to the invention. This STS anastomotic device essentially consists of two components, on the one hand the tubular body 12 with the upper and lower inner flange 11 formed in one piece therewith and, on the other hand, bush and outer flanges 300 constructed as an outer component. The outer component can, for example, be attached via serrations (not shown) at 302 to the tubular body. It will be clear that the outer component and the tubular body 12 can also be integrated in one piece. The STS anastomotic device will then be a one-piece device. Furthermore, it will be clear that, as shown by broken line 301, the outer flanges 300 can also be constructed in two parts, for example two cylindrical parts (cf. 314 in FIG. 17). Furthermore, it is also clearly apparent that outer component 300 can optionally also be dispensed with in its entirety, in which case the vessels 2 and 4 are then in direct contact with, and are pressed against, one another around the anastomotic.

FIG. 16 shows a further variant of an STS anastomotic device according to the invention. The STS anastomotic device according to FIG. 16 consists of two tubular bodies having an inner flange and outer flange formed in one piece therewith, it being possible for the respective outer flanges 215 to be joined to one another via a rotary connection 206, 207 allowing rotation about axis of rotation 200. Such a rotary connection can, in a simple form, comprise an annular rib 206 and annular recess 207, which are then able to engage in one another. If the rib 206 and recess 207 are of suitable design it is also possible with this arrangement to achieve a mutual coupling which counteracts taking apart in the axial direction of the axis of rotation 200. This can be implemented, for example, by designing the recess 207 as an undercut slit and making the rib 206 of corresponding shape, so that the latter can be accommodated with a tight fit in the slit 207. In the case of the embodiment according to FIG. 16, keeping the top and bottom half of the STS anastomotic device together can optionally be ensured, as a supplement to or replacement for the coupling action of the rib 206 and recess 207, by making use of essentially U-shaped clamping pieces 208 which hold the outer flanges together after having been slid thereon in accordance with arrow 209 and which allow the rotation of the bottom half and top half relative to one another around axis of rotation 200. With this arrangement the U-shaped clamping pieces can be constructed as one component or as several individual components. It is optionally possible to construct clamping piece 208 as a continuous or discontinuous ring.

FIG. 17 shows, in perspective view, yet a further variant of an STS anastomotic device according to the invention. As in the case of the embodiment according to FIG. 8, the outer flanges 314 are of cylindrically curved construction with an internal radius of curvature which is approximately equal to the external radius of curvature of the one vessel 2 and other vessel 4. The radii of curvature of the outer flanges can differ from one another, depending on those of the vessels 2, 4. The arms forming the inner flange are indicated by 311. Coupling flanges 312 are attached to the respective STS anastomotic devices directly at the outer flanges and/or tubular elements or via connection pieces 313. The join between vessels 2 and 4 can be produced by placing said coupling flanges 312 against one another and fixing to one another. For fixing the coupling flanges 312 to one another use can be made of clamps, as is indicated by 208 in FIG. 16, and/or of a slit/rib assembly, as shown by 207/206 in FIG. 16 and/or of other fixing means. If the coupling flanges 312 are of circular construction, rotation of the vessels 2, 4 with respect to one another about an imaginary join axis is possible.

FIGS. 18–22 show illustrative embodiments of ETE anastomoses.

The ETE anastomotic device shown in FIG. 18 essentially corresponds to the ETE anastomotic device shown in FIG. 4. The essential difference is that here the target vessel 2 is located in the extension of the graft vessel 4 and that the outer flange 15 has an essentially tubular shape and that the inner flange arms 11 extend essentially in the longitudinal direction of the target vessel, at least when fitted. Before fitting, the inner flange arms will point inwards, as is indicated by broken lines, in order to facilitate insertion of the inner flange into the target vessel. The pretension present in the inner flange arms 11 can be released in a manner corresponding to that in the case of the embodiment according to FIG. 4, after which said arms 11 are able to assume the position shown by continuous lines.

FIG. 19 shows a further variant of an ETE anastomotic device according to the invention. This ETE anastomotic device essentially shows great correspondence with the ETS anastomotic device in FIG. 6. The difference here is once again, as in the case of FIG. 18, that the outer flange is an essentially tubular body and that the inner flange arms extend essentially parallel to the target vessel when fitted. By extending the leg 210 of the coupling piece 27 it is possible to achieve a situation where those parts of the anastomotic device which come into contact with the bloodstream are virtually completely covered by blood vessel tissue.

FIG. 20 shows a variant of the ETE anastomotic device in FIG. 19. The difference here is that the tubular body 30 has been shaped to deflect outwards and that there is no longer extension of the leg 210. This ETE anastomotic device is, in particular, suitable for end-to-end joining of vessels of approximately equal diameter to one another.

FIG. 21 shows yet a further variant of an ETE anastomotic device, which is constructed in one piece. This ETE anastomotic device essentially displays great similarity to the ETS anastomotic device in FIG. 7a. As in the case of FIGS. 17 and 18, the essential difference from the comparable ETS anastomotic device is that the outer flange is constructed as a tubular body and that the inner flange arms run parallel to the target vessel, at least in the assembled state. The embodiment shown in FIG. 21 is likewise particularly suitable for joining vessels of approximately equal diameter to one another. Looking at FIG. 21 and FIGS. 7a to 7d, it will be clear that, corresponding to the variants shown in FIGS. 7b to 7d, three variants of the device shown in FIG. 21 are easily conceivable. However, just as in the case of FIGS. 7a to 7d, it will be clear that many further variants which fall within the essence of the invention are conceivable in the case of FIG. 21 as well.

FIG. 22 shows yet a further variant of an ETE anastomotic device, which is constructed in three parts. This ETE anastomotic device essentially displays similarity to the ETS anastomotic device in FIG. 5, except that the coupling piece 116 in FIG. 5 is dispensed with and has been replaced by a second tubular body 110 with an inner flange, in the form of arms 111, integral therewith and a second outer flange 114 integral with the bush 115. The outer flanges 114 are essentially of cylindrical construction in order to be able to enclose the end of a graft vessel or target vessel. The inner flange, in particular the arms 111, are likewise essentially cylindrical with the proviso that said arms have been stressed with a radial pretension, which can be released.

As should be clear on the basis of FIGS. 14–22, in these figures there is essentially no distinction between a graft vessel and a target vessel. The distinction here is more linguistic in order to be able to differentiate between one vessel and another vessel.

As should be clear in particular from FIGS. 14 and 16 it can be very useful, especially in the case of STS anastomotic devices, if an anastomotic device is used here which has freedom of rotation about a longitudinal axis extending through the connection openings. The reason for this is because the vessels to be joined to one another then still have some freedom of movement with respect to one another at the location of the join and are thus able to adapt to changing circumstances in the body and also to allow the vessels to assume different angles with respect to one another when making the joins, as a result of which kinking of the by-passes occurs less easily. However, it will be clear that in essence it is also possible to provide an ETE anastomotic device or an ETS anastomotic device with freedom of rotation, such that the one vessel, the graft vessel, is rotatable with respect to the other vessel, the target vessel, about a longitudinal axis passing through the connection opening of both vessels or one of the vessels. In the case of an ETS anastomotic device according to FIG. 13B, said longitudinal axis could be an axis as drawn in said figure, but the graft vessel which branches at an angle must then be of circular shape at the location of the join in a cross-sectional plane perpendicular to said axis. According to a fifth aspect, which can be considered completely independently of aspects 1 to 4 or in arbitrary combination with one or more of said aspects 1 to 4, the invention therefore relates to an anastomotic device comprising a first anastomotic fitting for fixing to the one vessel and a second anastomotic fitting for fixing to the other vessel, which anastomotic fittings are of essentially circular shape and can be rotatably joined to one another.

As should be clear from the above, the number of components, including the coupling means by means of which a graft vessel or target vessel can be fixed in place, can be made up of one or more components. In particular, a distinction can be made between the one-piece form, the two-piece form, the three-piece form, the four-piece form, the five-piece form and more than five-piece forms.

In the case of the one-piece form (see, for example, FIGS. 7a–e, 8, 21) graft vessel and target vessel are both fixed to a single component, use being made of the first aspect of the invention in the case of at least one of the vessels. The other vessel can optionally be attached to the same component in a different way. This will in general be the case with ETS and ETE anastomoses, where the target vessel is clamped in accordance with the first aspect of the invention and the graft vessel is attached to the same component in another way. However both (target vessel and graft vessel) can be attached to the same component in accordance with the first aspect of the invention in the case of both an ETS, an ETE and an STS anastomotic.

In the case of the two-part form (see, for example, FIGS. 6, 9a–b, 10a–b, 15, 16 (without optional component 208), 17, 19 and 20) there are two separate components which are joined to one another. With this arrangement it is possible that the graft vessel and the target vessel are each individually attached to a separate component first, but it is also possible that use is made of a separate inner and outer flange for attaching the target vessel, the graft vessel being attached directly to the tubular body or the outer flange. Coupling can then take place with the aid of, for example, snap-fit, hook and/or serrated profiles or other locking means, such as, for example, a bayonet fitting, which per se are integrated in said two components and are not separate. With this arrangement use is made of two components, the first aspect of the invention being used for at least one vessel coupling. Connections of this type are readily conceivable for ETS and ETE anastomoses, the procedure being carried out using an additional separate coupling piece. However, the vessel coupling can also operate in accordance with the first aspect of the invention for both vessels, it optionally being possible for one component to be attached to the target vessel and the other component to the graft vessel. In general this will be the case with STS anastomoses, but this is very readily possible and can offer major advantages with ETS and ETE anastomoses as well.

The three-part form (see, for example, FIGS. 2, 3, 4, 5, 14, 16 (with component 208), 18, 22) consists of three separate components, at least one vessel coupling operating in accordance with the first aspect of the invention. It can be the case that the graft vessel and the target vessel are each individually attached to a separate component first, after which a separate third component is used for joining the vessels together. It can also be the case that said third component is a common double outer flange (see, for example, FIGS. 14 and 22) or double inner flange. This three-part form can arise with STS anastomoses, but also with ETS and ETE anastomoses. Furthermore, in the case of the three-part form it is also conceivable that use is made of an individual inner and outer flange for attaching the target vessel, the graft vessel being attached to a separate, independent coupling piece. Coupling of the components can then take place with the aid of, for example, snap-fit, hook and/or serrated profiles or other locking means, such as, for example, a bayonet fitting, which can be integrated in the tubular body or the outer flange (and then thus not separate from these). This form appears very suitable for ETS and ETE anastomoses, although this form is also readily conceivable for STS anastomoses.

In the case of the four-part form (see, for example, FIG. 12 in combination with FIGS. 2–5) use is made of four components which are joined to one another, at least one vessel coupling according to the first aspect of the invention being provided. This form will usually consist of two individual components for, respectively, the target vessel and the graft vessel, it then being readily possible that use is made of the principles according to the first aspect of the invention for both vessels. After the two components have been attached per target vessel and graft vessel, the two pairs are coupled to one another by means of integral coupling means, such as, for example, snap-fit, hook and/or serrated profiles or other locking means, such as, for example, a bayonet fitting. The four-part form can arise with each of the three types of anastomotic device, but appears to be particularly attractive for STS anastomoses.

In the case of the five-part form use is made of five components which are joined to one another, at least the first aspect of the invention being employed. This system works in the same way as the four-part form, but use is made of an additional separate component for joining the parts attached to the target vessel and graft vessel to one another. This form is suitable for use with all types of anastomoses and is very attractive for STS anastomoses in particular.

In the case of the more than five-part forms use is made of more than five components which are joined to one another and where at least the first aspect of the invention is employed. This system works in the same way as the four-part form, but use is also made of several additional, independent components for joining the parts joined to the target vessel and graft vessel to one another. This form is suitable for use with all types of anastomoses and will occur in particular with STS anastomoses.

What is claimed is:

1. An anastomotic device for joining a graft vessel to a target vessel at a connection opening present therein, comprising:

an essentially tubular body having a bottom rim to be directed towards the target vessel;

an outer flange that is fitted or can be fitted on the outside of the tubular body and can be brought into contact, around the connection opening, with the outside of the wall of the target vessel; and an inner flange, formed on the tubular body, which in a attachment position projects outwards with respect to the tubular body and, overlapping the outer flange around the connection opening, can come into contact with the inside of the wall of the target vessel and which is bendable from an insertion position into said attachment position, wherein, in the insertion position, the projection of the inner flange on the plane spanned by the bottom rim of the tubular body is located essentially on and/or inside said bottom rim, such that the inner flange can be inserted through the connection opening in the target vessel, characterised in that, the inner flange is reversibly bent against a resilient force from the attachment position into the insertion position, which is a pretensioned position, and that the inner flange is fixed in said pretensioned insertion position in a manner such that the fixing can be released in order to cause the inner flange to bend back in the direction of the attachment position under the influence of the pretension.

2. Anastomotic device according to claim 1, wherein the outer flange is slidable in the longitudinal direction of the tubular body and/or in the direction of the inner flange and can be locked with respect to the tubular body and/or the inner flange by means of locking means.

3. Anastomotic device according to claim 2, for joining to a target vessel of the type where the connection opening has been made in the wall and wherein the distance from the outer flange to the outward-projecting inner flange is adjustable.

4. Anastomotic device according to claim 2, wherein the locking means comprise a mechanism involving serrations.

5. Anastomotic device according to claim 1, wherein the inner flange is made from a superelastic metal alloy or a thermally activated or activatable alloy with shape memory, such as a nickel-titanium alloy (for example Nitinol).

6. Anastomotic device according to claim 1, wherein the inner flange has a bending axis which extends tangentially with respect to the bottom rim of the tubular body and is located at the level of the inner periphery of the outer flange.

7. Anastomotic device according to claim 1, wherein the inner flange has a number of arms which are separated from one another by notches, cut-outs or folds and are arranged distributed around the periphery of the tubular body, the notches or cut-outs or folds preferably continuing as far as or beyond the outer flange.

8. Anastomotic device according to claim 1, wherein that face of the inner flange which in the free position faces towards the inner wall of the target vessel is provided with roughening or unevenness.

9. Anastomotic device according to claim 8, further comprising an inner flange which a continuous or discontinuous inner flange contact surface is intended to be brought into contact with the inside of the wall of the blood vessel around the opening, characterised in that the inner flange contact surface is cylindrically curved with a radius of curvature which is equal to or approximately equal to the internal circumferential radius of the target vessel at the location of the connection opening; or is equal to or approximately equal to the radius of curvature of the outer flange contact surface.

10. Anastomotic device according to claim 9, wherein the radius of curvature of the inner flange contact surface is in the range from 0.5 to 1.25 mm or in the range from 15–25 mm.

11. Anastomotic device preferably according to claim 1, wherein the anastomotic device, or at least the bottom rim of the tubular body thereof, has an essentially oval or elliptical shape/contour.

12. Anastomotic device according to claim 1, for joining a graft vessel to a target vessel at an opening present therein, optionally, an opening present in the wall thereof, comprising an outer flange of which an outer flange contact surface is intended to be brought into contact with the outside of the wall of the target vessel around the opening, characterised in that the outer flange contact surface is of cylindrically curved construction, preferably with a radius or curvature which is equal to or approximately equal to the external circumferential radius of the target vessel at the location of the connection opening.

13. Anastomotic device according to claim 12 wherein the outer flange contact surface has the shape of, essentially, a cylinder sector which extends over at most 180°.

14. Anastomotic device according to claim 12, the radius of curvature of the outer flange contact surface being in the range from 0.5 to 1.25 mm or in the range from 15 to 25 mm.

15. Anastomotic device according to claim 12, wherein the longitudinal edges (64) of the outer flange are constructed as support edges or are provided with outward-facing support ribs (65).

16. Anastomotic device according to claim 12 wherein the outer flange contact surface has the shape of, essentially, a cylinder sector which extends over from 150° to 180°.

17. Anastomotic device preferably according to claim 1, further comprising coupling means, optionally formed in one piece with the tubular body or the outer flange, for attaching the free end of the graft vessel to the tubular body or for attaching the anastomotic device to a further anastomotic device.

18. Anastomotic device according to claim 17, wherein the coupling means comprise an accessory, which can be at least partially inserted in the tubular body, having a passage for the graft vessel.

19. Anastomotic device according to claim 18, wherein the tubular body and/or the accessory preferably are/is provided with a stop which is arranged such that it prevents the accessory from being able to protrude beyond the bottom rim of the tubular body.

20. Anastomotic device according to claim 19, wherein the stop is arranged such that when the accessory is in the inserted position its bottom end reaches as far as the bottom rim.

21. Anastomotic device according to claim 17, wherein the coupling means have a series of passages for suture which are arranged around the periphery of the tubular body or the separate accessory and pass in the radial direction through the tubular body or the accessory, the passages preferably having a diameter of approximately 0.5 to 1.5 mm.

22. Anastomotic device according to claim 17, wherein the coupling means comprise a flexible and/or resilient ring which is sized such that the connection end of the graft vessel can be inserted through it and wrapped back over it, and wherein a peripheral groove, which opens inwards and in which the ring, together with part of the folded-back connection end of the graft vessel can be accommodated, preferably in a tight-fitting manner, is provided in an internal peripheral surface of the anastomotic device, preferably of the tubular body thereof.

23. Anastomotic device according to claim 22, wherein the peripheral groove opens obliquely downwards into the target vessel.

24. Anastomotic device according to claim 22, wherein two or more rod-shaped parts are fixed to the ring, which rod-shaped parts are essentially at right angles to the ring, extend in the axial direction thereof and are fixed at their other ends to a flexible sleeve.

25. Anastomotic device according to claim 17, wherein the coupling means comprise an outwardly tapering tube, which is sized such that the connection end of the graft vessel can be inserted through it and folded back over it, and a clamping ring which can be slid over the tube from the narrow end, with the folded-back part of the graft vessel lying between the ring and the tube, until the ring is firmly clamped.

26. Anastomotic device according to claim 1, wherein the graft vessel is joined at an angle which is not equal to 90°.

27. Anastomotic device according to claim 1, wherein the device is made from or coated with material which is inert with respect to the human or animal body.

28. Anastomotic device according to claim 1, wherein the inner flange and/or arms of the anastomotic device and/or those parts of the anastomotic device which come into contact with blood are made from and/or coated with materials which counteract blood clotting.

29. Anastomotic device for joining together two vessels at connection openings present therein, preferably according to claim 1, comprising a first anastomotic fitting for attachment to the one vessel of the vessels to be joined and a second anastomotic fitting for attachment to the other vessel of the vessels to be joined, wherein the anastomotic fittings are of essentially circular shape at the connection openings and can be joined to one another in a manner such that they are rotatable about an axis of rotation perpendicular to the connection openings.

30. Anastomotic device according to claim 29, wherein the one anastomotic fitting is provided on that side thereof which faces towards the other anastomotic fitting with a, preferably undercut, circular slit running around the connection opening and wherein the other anastomotic fitting is provided on that side thereof which faces the slit with a continuous or discontinuous circular rib running around the connection opening, which rib can be accommodated or is accommodated in the slit, preferably in a tight-fitting manner.

31. Anastomotic device according to claim 30, wherein the rib is a discontinuous rib which is made up of rib segments arranged distributed around the connection opening.

32. Anastomotic device according to claim 1, wherein the graft vessel is joined at an angle less than 70°.

* * * * *